US010420545B2

(12) United States Patent
Nobles et al.

(10) Patent No.: US 10,420,545 B2
(45) Date of Patent: Sep. 24, 2019

(54) SUTURING DEVICES AND METHODS FOR SUTURING AN ANATOMIC STRUCTURE

(71) Applicant: HeartStitch, Inc., Fountain Valley, CA (US)

(72) Inventors: Anthony A. Nobles, Fountain Valley, CA (US); Benjamin G. Brosch, Mission Viejo, CA (US); William Ettlinger Cohn, Bellaire, TX (US); Daniel W. Haines, Garden Grove, CA (US)

(73) Assignee: HeartStitch, Inc., Fountain Valley, CA (US)

( * ) Notice: Subject to any disclaimer, the term of this patent is extended or adjusted under 35 U.S.C. 154(b) by 0 days.

(21) Appl. No.: 15/645,438

(22) Filed: Jul. 10, 2017

(65) Prior Publication Data

US 2017/0303915 A1 Oct. 26, 2017

Related U.S. Application Data

(63) Continuation of application No. 14/400,309, filed as application No. PCT/US2013/040418 on May 9, 2013, now Pat. No. 9,706,988.
(Continued)

(51) Int. Cl.
A61B 17/04 (2006.01)
A61B 17/00 (2006.01)
(Continued)

(52) U.S. Cl.
CPC ...... A61B 17/0469 (2013.01); A61B 17/0057 (2013.01); A61B 17/0491 (2013.01);
(Continued)

(58) Field of Classification Search
CPC ... A61B 17/04; A61B 17/064; A61B 17/0401; A61B 2017/0409; A61B 17/0469;
(Continued)

(56) References Cited

U.S. PATENT DOCUMENTS 118,683 A 9/1871 Bruce
1,064,307 A 6/1913 Fleming
(Continued)

FOREIGN PATENT DOCUMENTS

AU 2003212025 8/2003
AU 2006251579 11/2006
(Continued)

OTHER PUBLICATIONS

U.S. Appl. No. 13/736,032, filed Jan. 7, 2013, Nobles et al.
(Continued)

Primary Examiner — Julianna N Harvey
Assistant Examiner — Christina Negrellirodriguez
(74) Attorney, Agent, or Firm — Knobbe, Martens, Olson & Bear LLP

(57) ABSTRACT

Suturing devices and systems used to close openings into a biological structure. The suturing device can comprise an elongate member having a proximal end, a distal end, one or more arms, and one or more needles. One or more sheaths may be used with the device to maintain or substantially maintain haemostasis while the device is used and while a procedure is performed in the biological structure.

28 Claims, 30 Drawing Sheets

Related U.S. Application Data

(60) Provisional application No. 61/646,188, filed on May 11, 2012, provisional application No. 61/715,123, filed on Oct. 17, 2012, provisional application No. 61/779,901, filed on Mar. 13, 2013.

(51) Int. Cl.
  *A61B 17/06* (2006.01)
  *A61B 17/34* (2006.01)
  *A61M 25/09* (2006.01)
  *A61B 17/02* (2006.01)

(52) U.S. Cl.
  CPC .. *A61B 17/06066* (2013.01); *A61B 17/06166* (2013.01); *A61B 17/3403* (2013.01); *A61B 17/3415* (2013.01); *A61B 17/3423* (2013.01); *A61B 17/3478* (2013.01); *A61M 25/09* (2013.01); *A61B 17/0485* (2013.01); *A61B 2017/0061* (2013.01); *A61B 2017/00243* (2013.01); *A61B 2017/00336* (2013.01); *A61B 2017/00349* (2013.01); *A61B 2017/00575* (2013.01); *A61B 2017/00623* (2013.01); *A61B 2017/00663* (2013.01); *A61B 2017/0237* (2013.01); *A61B 2017/0406* (2013.01); *A61B 2017/047* (2013.01); *A61B 2017/048* (2013.01); *A61B 2017/0414* (2013.01); *A61B 2017/0472* (2013.01); *A61B 2017/3405* (2013.01); *A61B 2217/005* (2013.01)

(58) Field of Classification Search
  CPC ...... A61B 2017/047; A61B 2017/0472; A61B 17/0482; A61B 17/0483
  USPC ............... 606/138, 139, 144, 145, 147, 148; 600/204
  See application file for complete search history.

(56) References Cited

U.S. PATENT DOCUMENTS

| | | |
|---|---|---|
| 1,822,330 A | 9/1931 | Ainslie |
| 1,989,919 A | 2/1935 | Everitt |
| 2,473,742 A | 6/1949 | Auzin |
| 2,548,602 A | 4/1951 | Greenburg |
| 2,637,290 A | 5/1953 | Sigoda |
| 2,738,790 A | 3/1956 | Todt, Sr. et al. |
| 2,849,002 A | 8/1958 | Oddo |
| 2,945,460 A | 7/1960 | Kagiyama |
| 3,241,554 A | 3/1966 | Coanda |
| 3,292,627 A | 12/1966 | Harautuneian |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,994,070 A | 2/1991 | Waters |
| 5,002,531 A | 3/1991 | Bonzel |
| 5,021,059 A | 6/1991 | Kensey et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,176,691 A | 1/1993 | Pierce |
| 5,192,301 A | 3/1993 | Kamiya et al. |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |

(56) References Cited

U.S. PATENT DOCUMENTS

| | | |
|---|---|---|
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safer et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Amnbrosio |
| 5,700,273 A | 12/1997 | Buelna et al. |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |

(56) References Cited

U.S. PATENT DOCUMENTS

| | | |
|---|---|---|
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,786,913 B1 | 9/2004 | Sancoff |
| 6,978,176 B2 | 1/2005 | Lattouf |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,469,975 B2 | 6/2013 | Nobles et al. |
| 8,496,676 B2 | 7/2013 | Nobles et al. |
| 8,540,736 B2 | 9/2013 | Gaynor et al. |
| 8,568,427 B2 | 10/2013 | Nobles et al. |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,398,907 B2 | 7/2016 | Nobles et al. |
| 9,706,988 B2 | 7/2017 | Nobles et al. |
| 2001/0031973 A1 | 10/2001 | Nobles et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0111653 A1 | 5/2002 | Foerster |
| 2002/0087178 A1 | 7/2002 | Nobles et al. |
| 2002/0096183 A1 | 7/2002 | Stevens et al. |
| 2002/0128598 A1 | 9/2002 | Nobles |

(56) References Cited

U.S. PATENT DOCUMENTS

| | | |
|---|---|---|
| 2002/0128684 A1 | 9/2002 | Foerster |
| 2002/0183787 A1 | 12/2002 | Wahr et al. |
| 2003/0078601 A1 | 4/2003 | Skikhman et al. |
| 2003/0144673 A1 | 7/2003 | Onuki et al. |
| 2003/0149448 A1 | 8/2003 | Foerster et al. |
| 2003/0167062 A1 | 9/2003 | Gambale et al. |
| 2003/0171760 A1 | 9/2003 | Gambale |
| 2003/0181926 A1 | 9/2003 | Dana et al. |
| 2003/0208209 A1 | 11/2003 | Gambale et al. |
| 2004/0044365 A1 | 3/2004 | Bachman |
| 2004/0059351 A1 | 3/2004 | Eigler et al. |
| 2004/0093031 A1 | 5/2004 | Burkhart et al. |
| 2004/0097968 A1 | 5/2004 | Sikikhman et al. |
| 2004/0102797 A1 | 5/2004 | Golden et al. |
| 2004/0098050 A1 | 8/2004 | Foerster et al. |
| 2004/0153116 A1 | 8/2004 | Nobles |
| 2004/0210238 A1 | 10/2004 | Nobles et al. |
| 2004/0236356 A1 | 11/2004 | Rioux et al. |
| 2004/0260298 A1 | 12/2004 | Kaiseer et al. |
| 2005/0033319 A1 | 2/2005 | Gambale et al. |
| 2005/0033361 A1 | 2/2005 | Galdonik et al. |
| 2005/0070923 A1 | 3/2005 | McIntosh |
| 2005/0149066 A1* | 7/2005 | Stafford ............. A61B 17/0057 606/144 |
| 2005/0187575 A1 | 8/2005 | Hallbeck et al. |
| 2005/0203564 A1 | 9/2005 | Nobles |
| 2005/0240226 A1 | 10/2005 | Foerster et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2005/0288688 A1 | 12/2005 | Sakamoto et al. |
| 2006/0047314 A1 | 3/2006 | Green |
| 2006/0052813 A1 | 3/2006 | Nobles |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0271074 A1 | 11/2006 | Ewers et al. |
| 2006/0282088 A1 | 12/2006 | Ryan |
| 2006/0282102 A1 | 12/2006 | Nobles et al. |
| 2006/0287657 A1 | 12/2006 | Bachman |
| 2007/0005081 A1 | 1/2007 | Findlay, III et al. |
| 2007/0010829 A1 | 1/2007 | Nobles et al. |
| 2007/0032798 A1 | 2/2007 | Pantages et al. |
| 2007/0043385 A1 | 2/2007 | Nobles et al. |
| 2007/0118151 A1 | 5/2007 | Davidson |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0188873 A1 | 8/2008 | Speziali |
| 2008/0228201 A1 | 9/2008 | Zarbatany |
| 2008/0234729 A1 | 9/2008 | Page et al. |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0287183 A1 | 11/2009 | Bishop et al. |
| 2009/0312783 A1* | 12/2009 | Whayne ......... A61B 17/320016 606/190 |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0087838 A1 | 4/2010 | Nobles et al. |
| 2010/0100167 A1 | 4/2010 | Bortlein et al. |
| 2011/0190793 A1 | 8/2011 | Nobles et al. |
| 2011/0202077 A1 | 8/2011 | Chin et al. |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2013/0103056 A1 | 4/2013 | Chu |
| 2013/0238001 A1 | 9/2013 | Nobles et al. |
| 2013/0261645 A1 | 10/2013 | Nobles et al. |
| 2014/0148825 A1 | 5/2014 | Nobles et al. |
| 2014/0163585 A1 | 6/2014 | Nobles et al. |
| 2014/0303654 A1 | 10/2014 | Nobles et al. |
| 2015/0374351 A1 | 12/2015 | Nobles et al. |
| 2016/0007998 A1 | 1/2016 | Nobles et al. |
| 2016/0151064 A1 | 6/2016 | Nobles |
| 2016/0302787 A1 | 10/2016 | Nobles |
| 2017/0042534 A1 | 2/2017 | Nobles |
| 2017/0245853 A1 | 8/2017 | Nobles |
| 2017/0296168 A1 | 10/2017 | Nobles |

FOREIGN PATENT DOCUMENTS

| | | |
|---|---|---|
| AU | 2006262498 | 1/2007 |
| CA | 2323084 | 12/2006 |
| CN | 195341 | 2/2005 |
| CN | 1654016 A | 8/2005 |
| CN | 101027001 | 8/2007 |
| CN | 101242785 A | 8/2008 |
| CN | 101495049 | 12/2010 |
| CN | 101257852 | 8/2011 |
| CN | ZL 201280029608.6 | 10/2016 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 0 983 026 | 3/2002 |
| EP | 1 196 093 | 4/2002 |
| EP | 0 941 698 | 5/2005 |
| EP | 0 983 027 | 12/2005 |
| EP | 1 804 677 | 7/2007 |
| EP | 1 570 790 | 11/2008 |
| EP | 2 011 441 | 1/2009 |
| FR | 2 701 401 | 8/1994 |
| HK | 1036395 | 5/2005 |
| JP | A 9507398 | 7/1997 |
| JP | 09-266910 A | 10/1997 |
| JP | H10-43192 | 2/1998 |
| JP | 2001-524864 | 12/2001 |
| JP | 2002-500531 | 1/2002 |
| JP | 2003-139113 A2 | 5/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 4399035 | 10/2009 |
| JP | 2009-261960 | 11/2009 |
| JP | 2010-522625 | 7/2010 |
| JP | 2011-067251 | 4/2011 |
| JP | 5848125 | 12/2015 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |

(56) References Cited

FOREIGN PATENT DOCUMENTS

| WO | WO 97/27807 | 8/1997 |
|---|---|---|
| WO | WO 97/40738 | 11/1997 |
| WO | WO 98/12970 | 4/1998 |
| WO | WO 98/52476 | 11/1998 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 08/121738 | 10/2008 |
| WO | WO 09/081396 | 7/2009 |
| WO | WO 09/137766 | 11/2009 |
| WO | WO 11/094619 | 8/2011 |
| WO | WO 11/137224 | 11/2011 |
| WO | WO 12/142338 | 10/2012 |
| WO | WO 13/170081 | 11/2013 |
| WO | WO 15/002815 | 1/2015 |
| WO | WO 15/085145 | 6/2015 |
| WO | WO 17/180092 | 10/2017 |

OTHER PUBLICATIONS

U.S. Appl. No. 09/080,823, filed May 18, 1998, Nobles.
U.S. Appl. No. 09/080,436, filed May 18, 1999, Nobles.
Advances in Vascular Surgery, by John S. Najarian, M.D. and John P. Delaney, M.D., copyright 1983 by Year Book Publishers, Inc. at pp. 94,95,96, and 224.
Cardio Medical Solutions, Inc. brochure titled: "Baladi Inverter for Clamp less Surgery"—Undated.
Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.
Current Therapy in Vascular Surgery, 2nd edition, by Calvin B. Ernst, M.D. and James C. Stanley, M.D., copyright 1991 by B.C. Decker, Inc., at pp. A and 140.
Eskuri, A., The Design of a Minimally Invasive Vascular Suturing Device, Thesis submitted to Rose-Hulman Institute of Technology, Nov. 1999.
Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.
Nursing the Open-Heart Surgery Patient, by Mary Jo Aspinall, R.N., M.N., copyright 1973 by McGraw Hill, Inc., at pp. 216 and 231.
Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.
Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.
Techniques in Vascular Surgery, by Denton A. Cooley, MD. and Don C. Wukasch, MD., copyright 1979 by WB. Saunders Co., at pp. 38,57,86,134,156, and 184.
The problem: Closing wounds in deep areas during laparoscopic operations The solution: REMA Medizintechnik GmbH (no date).
Vascular Access, Principles and Practice, 3rd edition, by Samuel Eric Wilson, MD., copyright 1996, 1988,1980 by Mosby-Year Book, Inc., pp. 89 and 159.
Vascular and Endovascular Surgery, by Jonathan D. Beard and Peter Gainers, copyright 1998 by W. B. Saunders Co., Ltd, p. 414.
Vascular Surgery, 3rd edition, vol. 1, by Robert B. Rutherford, MD., copyright 1989, 1984, 1976 by W. B.SaundersCo., at pp. 347, 348, 354, 594, 607, 622, 675, 677, 680, 698, 700, 721, 727, 735, and 829.
Vascular Surgery, 4th edition by Robert B. Rutherford, MD., copyright 1995,1989,1976, by W.B. Saunders Co., vol. 1, at pp. 400-404, 661, and A.
Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.
Vascular Surgery, by Robert B. Rutherford, M.D. copyright1977 by WB. Saunders Co., at pp. 334 and 817.
International Preliminary Report on Patentability re PCT/US2013/040418, dated Nov. 11, 2014.
International Search Report and Written Opinion of PCT/US2013/040418, dated Jul. 26, 2013.
European Extended Search Report, re EP Application No. 13787169.5, dated Feb. 1, 2016.

* cited by examiner

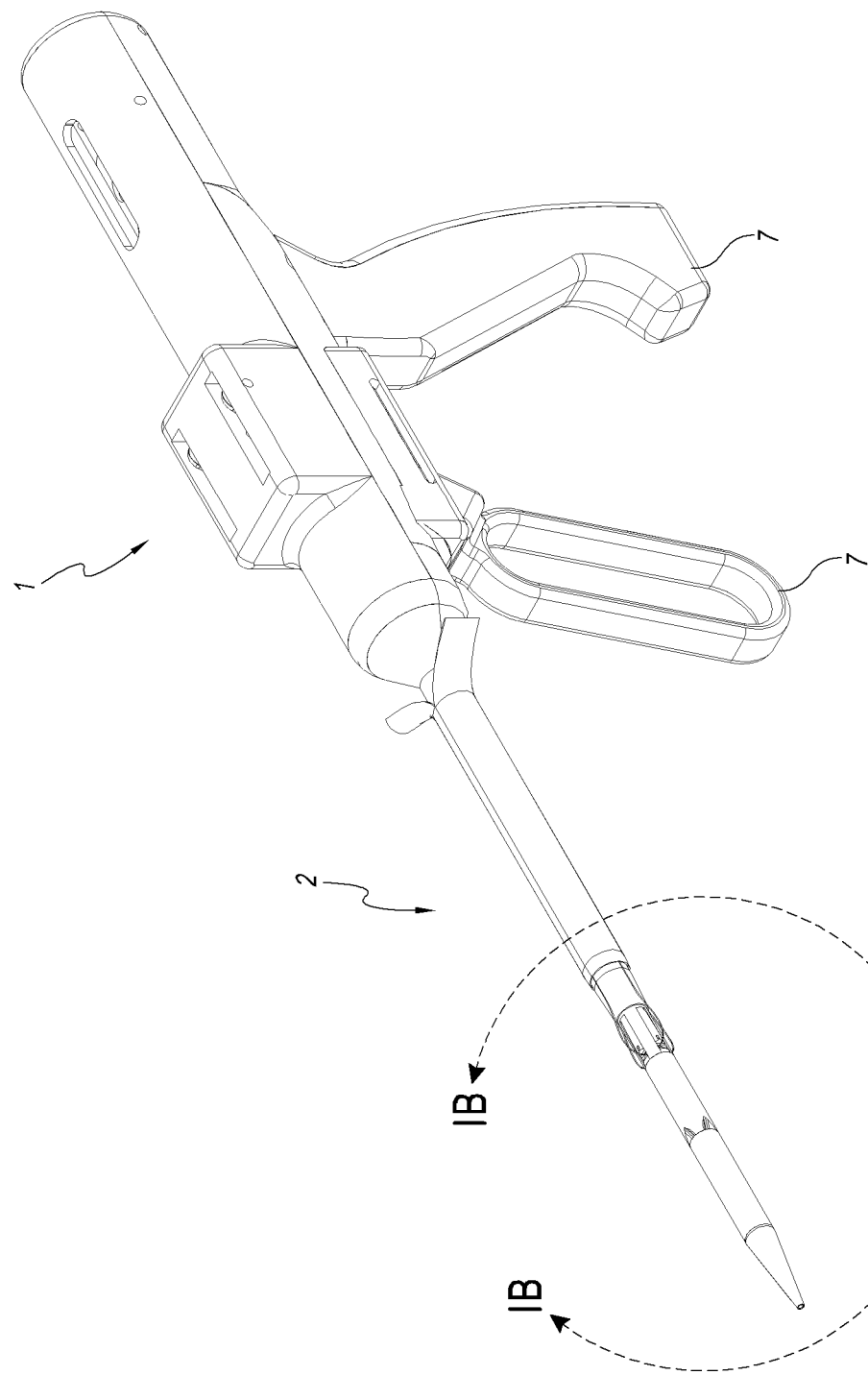
FIG. IA

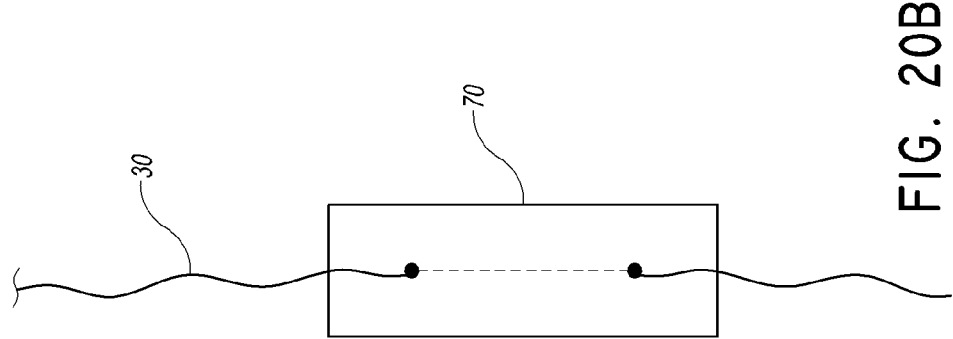
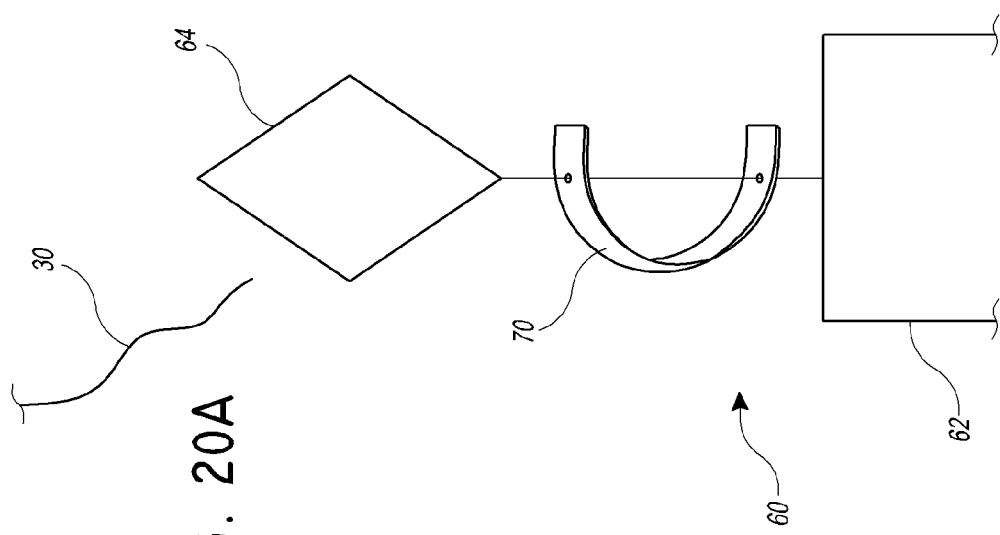

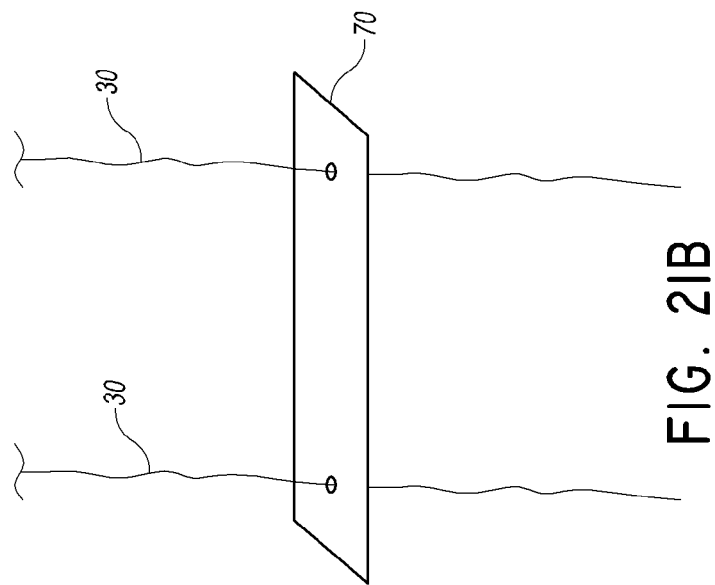
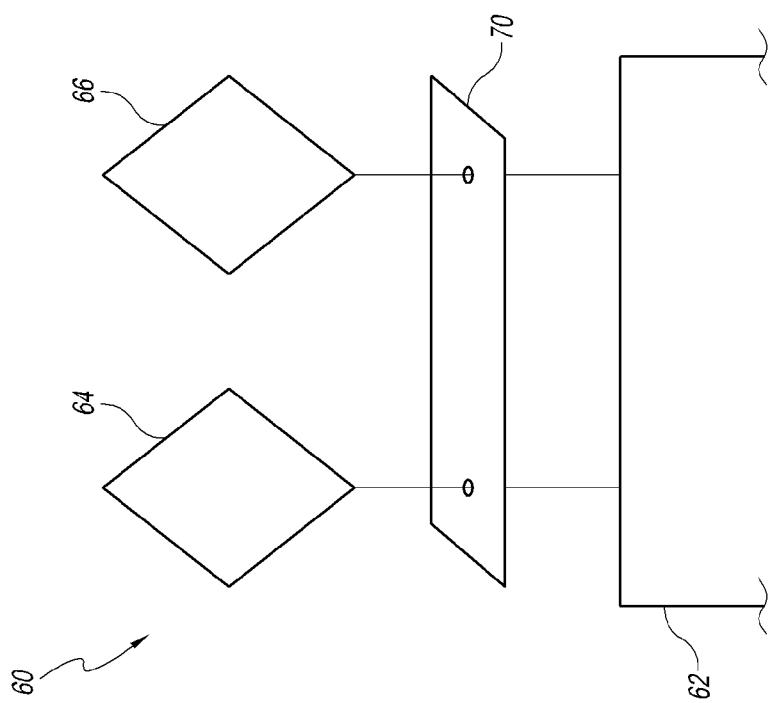

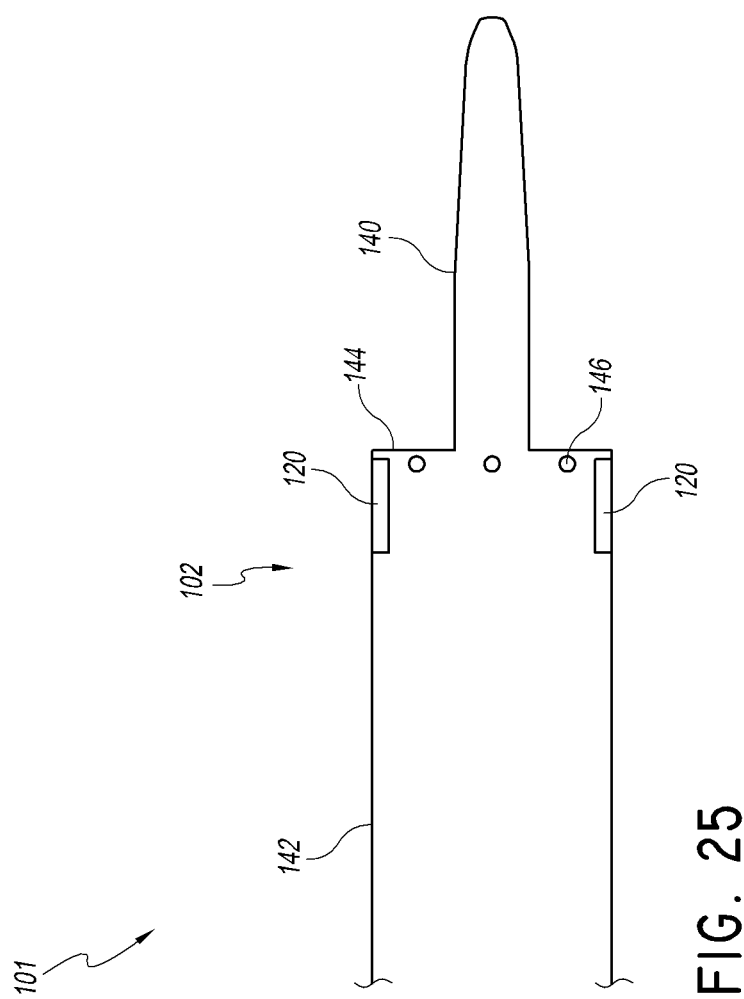

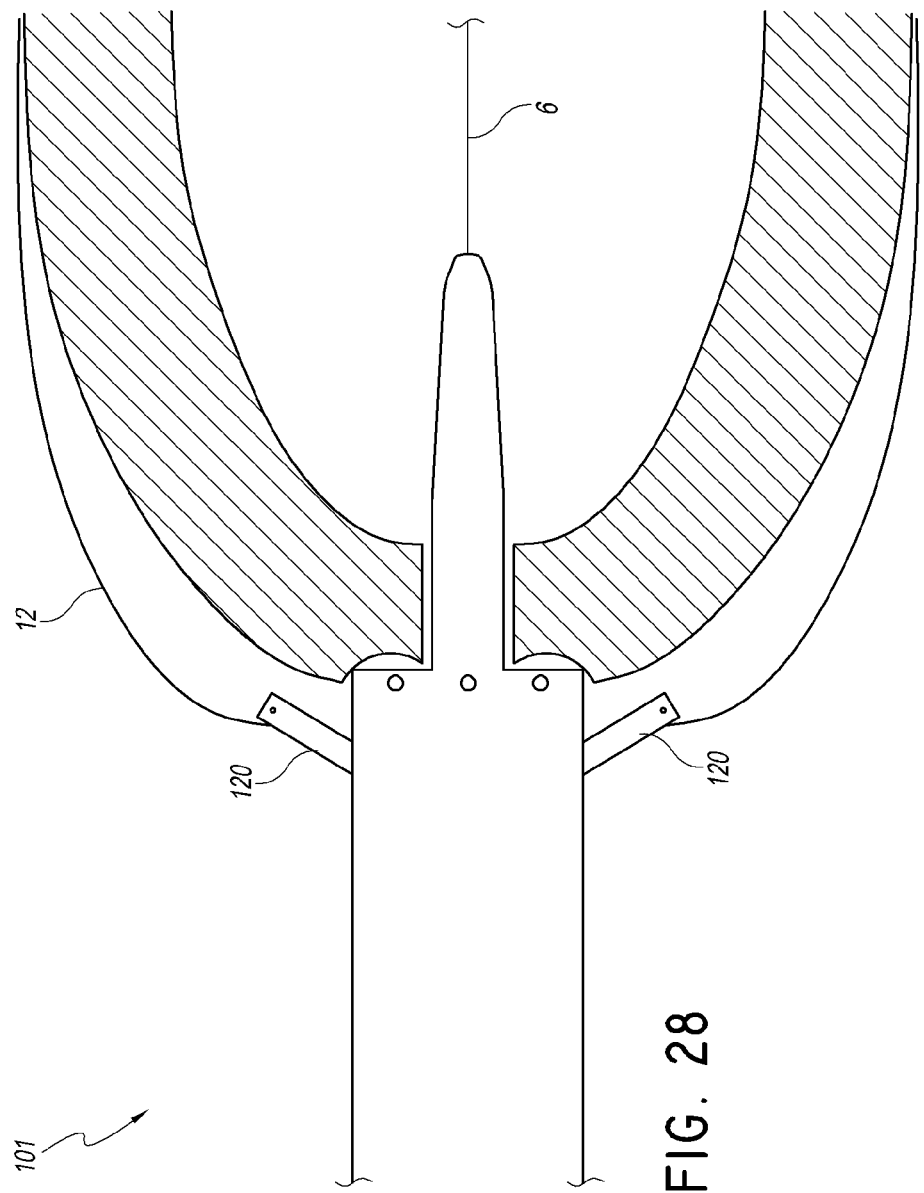

SUTURING DEVICES AND METHODS FOR SUTURING AN ANATOMIC STRUCTURE

CROSS-REFERENCE TO RELATED APPLICATIONS

This application is a continuation of U.S. patent application Ser. No. 14/400,309 filed Nov. 10, 2014, titled "SUTURING DEVICES AND METHODS FOR SUTURING AN ANATOMIC STRUCTURE", which is a U.S. National Phase of International Patent Application No. PCT/US2013/040418, filed May 9, 2013, titled "SUTURING DEVICES AND METHODS FOR SUTURING AN ANATOMIC STRUCTURE", which claims priority to U.S. Provisional Application No. 61/779,901, filed Mar. 13, 2013; U.S. Provisional Application No. 61/715,123, filed Oct. 17, 2012; and U.S. Provisional Application No. 61/646,188, filed May 11, 2012, the contents of all of which are hereby incorporated by reference herein.

TECHNICAL FIELD

Embodiments of the present invention relate to suturing devices and methods. Some embodiments relate to suturing devices and methods for suturing an anatomic structure, such as a heart.

BACKGROUND

Health practitioners frequently use sutures to close various openings such as cuts, punctures, and incisions in various places in the human body. Generally, sutures are convenient to use and function properly to hold openings in biological tissue closed thereby aiding in blood clotting, healing, and prevention of scarring.

There are some circumstances under which it is not feasible to use conventional sutures and suturing methods to close an opening. Additionally, there are some circumstances under which the use of conventional sutures and suturing methods require invasive procedures that subject a patient to risk of infection, delays in recovery, increases in pain, and other complications.

SUMMARY OF THE DISCLOSURE

Embodiments of suturing devices used to suture closed openings into a biological structure while maintaining or substantially maintaining haemostasis are described herein. The suturing devices and methods can also be used to place sutures prior to a surgical procedure and to prepare access for the procedure while maintaining or substantially maintaining haemostasis. The placed sutures can then be used to tighten an opening while any devices or tools are withdrawn, closing the opening while the final device or tool leaves the opening such that the opening is never without a device or tool inside it during the course of the procedure.

In the embodiments described herein, the disclosed devices are used to place sutures to close an opening into a heart, although they are not limited to applications within a heart. The heart can be accessed through a sternotomy or limited thoracotomy, or alternatively the device can pass through a trocar or other element into the thoracic cavity and then be led toward the opening in the heart, typically by following a guide wire. In some embodiments, the opening is a puncture made at or near the apex of the heart. The puncture can also be made at other areas of the heart. In some embodiments, suturing devices and methods disclosed herein can be used to minimize the collection of fluid between the heart and the pericardial sac that surrounds the heart.

In some embodiments, a suturing system can include a suturing device having an elongate body with a proximal end and a distal end, and a plurality of arms near the distal end. Each arm can be configured to move between a first position in which the arm is retracted within the elongate body and a second position in which the arm has a free end extending away from the elongate body. Each arm can have at least one suture mount at the free end. The device can also have a plurality of needles, each needle configured to move between a retracted position in which the needle is within the elongate body to a deployed position in which the distal point of the needle extends out of the elongate body and into a corresponding suture mount.

The system can also include a first sheath adapted to surround at least a portion of the elongate body, a second sheath adapted to surround at least a portion of the first sheath, and a plurality of suture portions. Each suture portion can have a suture end releasably retained within a suture mount of a corresponding arm, and each suture portion can extend from a corresponding suture end, between the first sheath and the second sheath, to a position proximal to at least the second sheath.

Methods of use are also described. In some embodiments, a suturing system can be delivered through a heart wall, and the suturing system can include a suturing device with an elongate body having a proximal end and a distal end, the suturing device also having a distal section that extends through the heart wall and into the heart once the suturing system is delivered. The suturing device can also have a plurality of arms positioned outside of the heart and a plurality of needles positioned inside the heart once the suturing system is delivered. The suturing system can also include a first sheath positioned over the suturing device, a distal end of the first sheath being proximal to the plurality of arms once the suturing system is delivered, and a second sheath positioned over the first sheath.

The plurality of arms can be extended from the elongate body of the suturing device, each of the arms carrying a suture portion having a suture end releasably retained in a respective arm, each suture portion extending from its respective arm proximally between the first sheath and the second sheath to a location outside of the patient. The plurality of arms can be positioned against the outside surface of the heart, and the plurality of needles can be advanced from the elongate body through the heart wall, each needle aligned with a respective arm and engaging a respective suture end carried by the respective arm. The plurality of needles can be retracted through the heart wall to draw the respective suture ends through the heart wall and the arms can be retracted into the elongate body of the suturing device while maintaining a distal section of the elongate body within the heart. The first sheath positioned around the elongate body can be advanced into the opening in the heart wall and the elongate body can be withdrawn from the heart wall while leaving the first sheath within the heart wall, the withdrawing of the elongate body drawing the suture ends engaged by the needles through a lumen of the first sheath to a location outside of the patient.

In some embodiments, a suturing device for suturing an opening in a heart wall can include an elongate body with a proximal end and a distal end, a first section at the distal end, a second section proximal to the first section, and a distally facing body surface between the first and second sections. The second section can have a larger outer dimension than the first section and the distally facing body surface can be configured to press against an external surface of a heart when the first section is advanced into the opening in the heart. The device can also include a plurality of arms near the distal end in the second section, each arm configured to move between a first position wherein the arm is retracted within the elongate body, and a second position wherein the arm has a free end extending away from the elongate body. Each arm has at least one suture mount at the free end and configured to releasably retain a suture portion. The device can also include a plurality of needles, each needle configured to move between a retracted position in which the needle is within the elongate body to a deployed position in which a distal point of the needle extends out of the elongate body and into a suture mount.

In some embodiments, an elongate device can be delivered through a heart wall such that a distal section of the device is positioned within the heart. Fluid exiting the heart along the distal section of the elongate device and through the heart wall can be removed. The removal can include the step of causing the fluid to flow through at least one opening positioned on the elongate device on an outside of the heart to remove fluid that may accumulate between the outside of the heart and the pericardial sac.

In some embodiments, a suturing device can include an elongate body with a proximal end and a distal end, the distal end of the elongate body configured to be delivered through a heart wall into a heart. The device can also include a plurality of arms near the distal end, each arm configured to move between a first position in which the arm is retracted within the elongate body and a second position in which the arm has a free end extending away from the elongate body. Each arm can have at least one suture mount at the free end and configured to releasably retain a suture portion. Each arm can also have a proximal side configured to engage the pericardial sac as the arm moves from the first position to the second position, and each arm in its second position can be configured to be positioned along an outer surface of the heart. The device can also include a plurality of needles, each needle configured to move between a retracted position in which the needle is within the elongate body to a deployed position in which a distal point of the needle extends out of the elongate body and into a suture mount, passing through the heart wall when the arms are positioned along an outer surface of the heart.

In some embodiments, a suturing device having an elongate body can be delivered through a heart wall such that a distal section of the device is positioned within the heart. The device can have a plurality of arms and a plurality of needles, and each arm can be moved from a first position wherein the arm is retracted within the elongate body to a second position wherein the arm has a free end extending away from the elongate body. The arms can engage the pericardial sac and move it away from an outer surface of the heart as they move to their second positions. Each arm can have at least one suture mount at the free end releasably retaining a suture portion, and the plurality of needles can be moved from a retracted position in which needles are within the elongate body to a deployed position in which distal points of the needles extend out of the elongate body, through the heart wall and into a suture mount of a corresponding arm.

In some embodiments, an opening in a heart can be closed by inserting four sutures through tissue of the heart wall such that each suture has an end that runs through the opening in the heart and an end that runs outside of the heart. The four sutures can include a first pair and a second pair of sutures, and the sutures of the first pair can be positioned opposite each other with respect to the opening in the heart and the sutures of the second pair can be positioned opposite each other with respect to the opening in the heart. A first pledget can be attached to a first end of a first suture and a second pledget can be attached to a first end of a second suture, where the first suture and a third suture make up the first pair, and the second suture and a fourth suture make up the second pair. The ends of the first pair that run through the opening of the heart can be secured together, and the ends of the second pair that run through the opening of the heart can be secured together. At least one of the ends that run outside the heart of each pair can then be pulled.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures:

FIG. 1A is a perspective view of one embodiment of a suturing device.

FIG. 20A is a schematic view of one embodiment of a threader.

FIG. 20B is a schematic view of a pledget having been threaded with the threader of FIG. 20A.

FIG. 21A is a schematic view of one embodiment of a threader.

FIG. 21B is a schematic view of a pledget having been threaded with the threader of FIG. 21A.

FIG. 25 is a side view of a distal assembly of one embodiment of a suturing device.

FIG. 28 is a schematic representation as in FIG. 27 showing the arms extended.

DETAILED DESCRIPTION OF SPECIFIC EMBODIMENTS

Figure 1B:
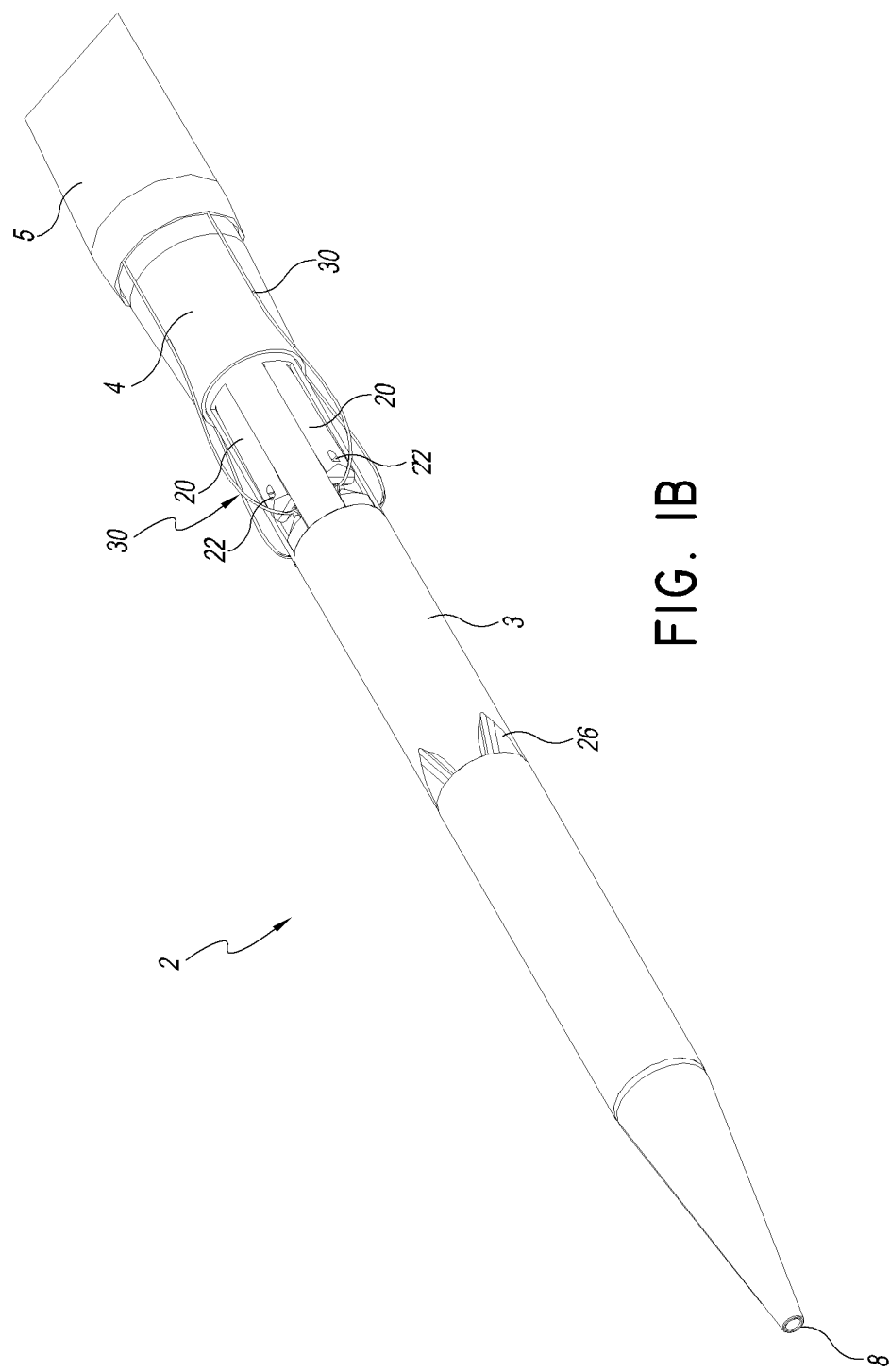
FIG. 1B is a perspective view of a distal assembly of one embodiment of a suturing device.

Embodiments of suturing devices used to suture closed openings into a biological structure while maintaining or substantially maintaining haemostasis are described herein. The suturing devices and methods can also be used to place sutures prior to a surgical procedure and to prepare access for the procedure while maintaining or substantially maintaining haemostasis. The placed sutures can then be used to tighten an opening while any devices or tools are withdrawn, closing the opening while the final device or tool leaves the opening such that the opening is never without a device or tool inside it during the course of the procedure.

In the embodiments described herein, the disclosed devices are used to place sutures to close an opening into a heart, although they are not limited to applications within a heart. In some embodiments, the opening is a puncture made at or near the apex of the heart. The puncture can also be made at other areas of the heart. The heart can be accessed through a sternotomy or limited thoracotomy, or alternatively the device can pass through a trocar or other element into the thoracic cavity and then be led toward the puncture in the heart, typically by following a guide wire.

A heart is surrounded by a pericardial sac (or pericardium), and in order to puncture into the heart the pericardium must also be punctured or cut and moved out of the way. Accessing the heart in this manner presents a risk that blood may leak through the opening and collect between the pericardium and the heart wall. This blood can put pressure against the heart and in some cases can cause a cardiac tamponade. In some embodiments described herein, the device can be used to limit the risk of blood collecting between the pericardium and the heart wall. This can be achieved by creating a space outside of the heart where blood can collect without running between the pericardium and the heart, and by creating a flow path from the space and into the device. In some embodiments, a negative pressure can be used to draw blood from the space and into the device.

In some embodiments described herein, the device can be used to limit the risk of blood collecting between the pericardium and the heart wall by suturing the opening closed with sutures that pass through the heart wall but not through the pericardium. The pericardium can thereby remain loose around the heart wall, blood can more easily drain out, and the pericardium can be sutured closed after blood has drained out.

In some embodiments, the suturing devices can be used to close or reduce a variety of other tissue openings, lumens, hollow organs or natural or surgically created passageways in the body. In some embodiments, the suturing devices can be used to suture prosthetics, synthetic materials, or implantable devices in the body. For example, the devices can be used to suture a pledget within the body.

Further details of suturing devices and methods that may be used to suture an opening in a heart can be found in U.S. Patent Publication No. 2011/0190793 A1, published Aug. 4, 2011, which is hereby incorporated by reference in its entirety. Features and procedures described in the aforementioned publication can be incorporated into the embodiments described herein.

FIGS. 1A and 1B illustrate perspective views of one embodiment of a suturing device 1. FIG. 1A is an embodiment of the entire device, and FIG. 1B illustrates a section of a distal assembly 2 of the device. The device can be used to insert sutures through the outer wall of a heart in anticipation of a surgical procedure within the heart, while maintaining haemostasis. The device has a proximal and a distal end. At the distal end, the device can have a guide wire lumen 8, which can allow the device to follow a guide wire to a desired position. At the proximal end, the suturing device can comprise one or more handles 7 with various mechanisms that can be used to control the elements of the distal assembly. Further details regarding handles and associated components, including actuator rods, are provided in U.S. Patent Application Publication No. 2008/0269786, published on Oct. 30, 2008, which is hereby incorporated by reference herein in its entirety.

The device can comprise an elongate body 3 which can include a plurality of suture arms 20. The suture arms 20 can move from a retracted position, as illustrated, in which the suture arms are at least partially within the elongate body 3, to an extended position, described and illustrated below in which the suture arms extend outward from the elongate body. The suture arms can also be positioned at varying angles from each other around the circumference of the elongate body. The illustrated embodiment has four suture arms 20 spaced 90 degrees apart. In some embodiments, there may be more suture arms spaced varying degrees apart. In some embodiments, there may be just one suture arm, which can be rotated about an opening in the heart to place multiple sutures around the opening. For purposes of closing the opening, it can be desirable to have an even number of suture arms, such as 2, 4, 6, or 8, each suture arm part of a pair with another suture arm spaced 180 degrees apart around the circumference of the elongate body. In some embodiments, the device can also have an odd number of suture arms. If just a single suture arm is used to position multiple sutures around the opening, the sutures can be positioned in pairs spaced 180 degrees apart around the opening.

The suture arms 20 can comprise one or more suture mounts or clasps 22 at a distal end. The suture clasps 22 can be adapted to releasably retain a suture portion 30. In some embodiments, the suture clasps can releasably retain a suture portion 30 while the suture arms 20 are in the retracted position and in the extended position. In some embodiments, as illustrated, the suture clasps may not retain a suture portion until the suture arms move toward the extended position. In some embodiments, a suture end may be retained in the suture clasps. In some embodiments, the suture clasps may retain a portion of suture that is not the suture end.

When the device is assembled, it can be pre-loaded with a first sheath 4 (for example an 18 french sheath) that surrounds at least a portion of the elongate body and a second sheath 5 surrounding at least a portion of the first sheath 4. In some embodiments, as illustrated, a distal end of the first sheath 4 can extend to a position just proximal to the suture arms, thereby allowing the suture arms to move into the extended position or into the retracted position. The suture portions 30 can run outside of the first sheath 4 and through the second sheath 5 to a position proximal to at least the second sheath 5. The second sheath can help confine the suture portions such that they do not get tangled or otherwise interfere with a procedure, described below. In some embodiments, the second sheath 5 is shorter than first sheath 4. In some embodiments, the second sheath 5 can be a peel-away sheath that can be removed from around the first sheath and around the suturing device.

The device can also include suture catch mechanisms (referred to herein as needles), described below, that can retrieve sections of suture from the suture clasps 22. In some embodiments, the device can include one or more needle exit channels 26, from which the needles can exit an interior of the elongate body 3 in order to reach the suture clasps 22. In some embodiments, there can be an equal number of needle exit channels 26 as there are suture arms 20, and the needle exit channels can be configured to align with a corresponding suture arm.

Figure 2:
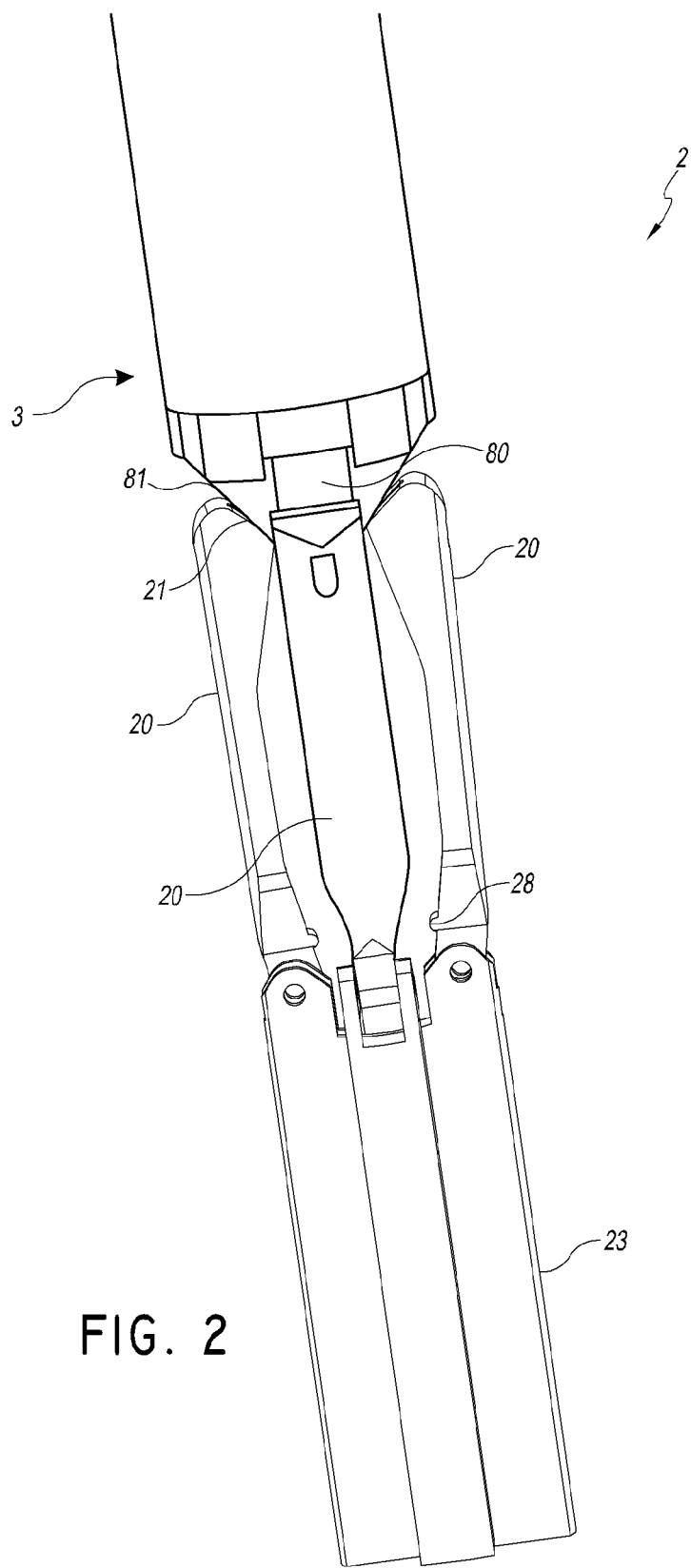
FIG. 2 is a perspective view of a portion of a suturing device showing suture arms in a retracted position and with certain external components not illustrated.
Figure 3:
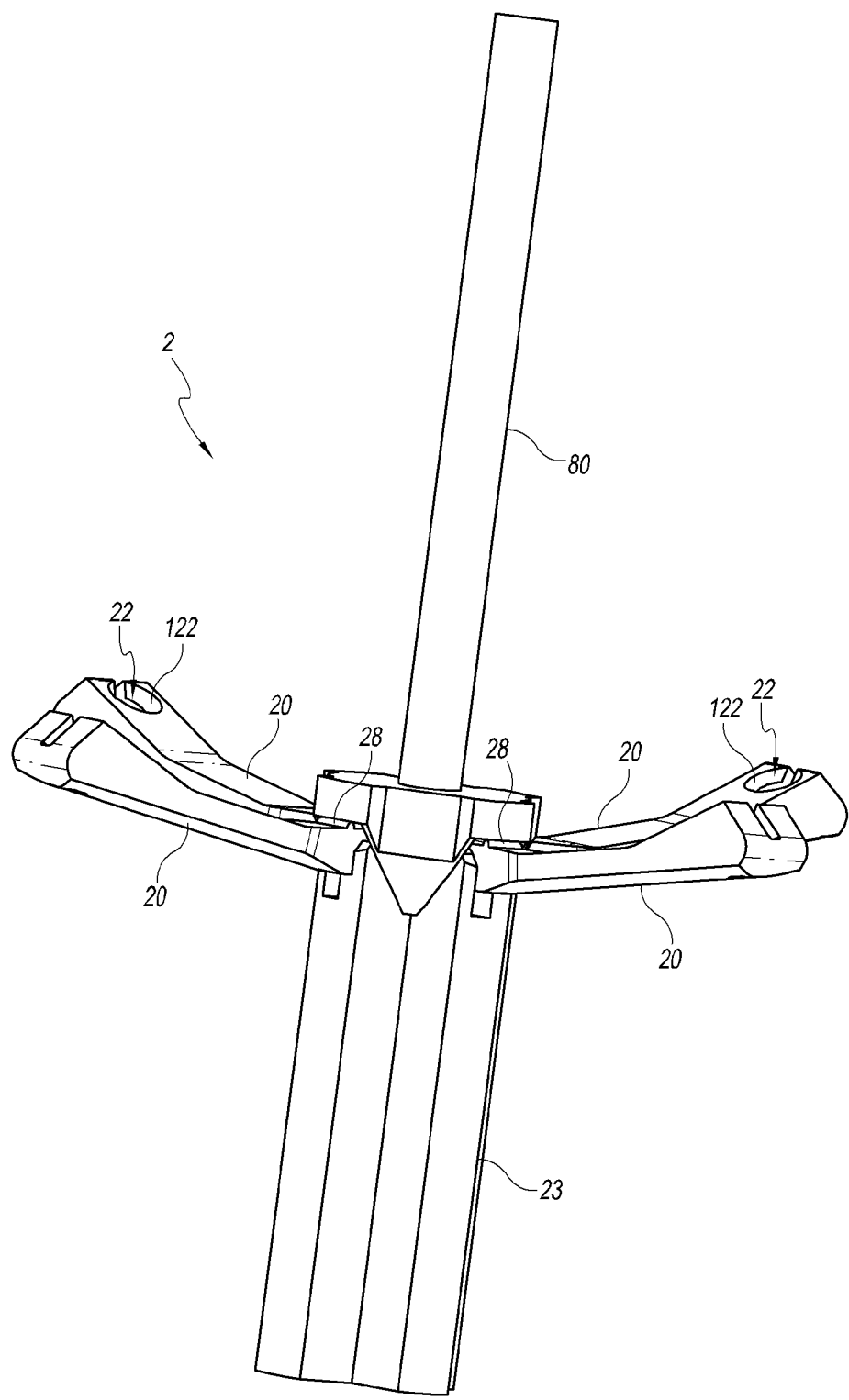
FIG. 3 is a perspective view of a portion of a suturing device showing suture arms in an extended position and with certain external components not illustrated.

FIGS. 2 and 3 illustrate the suture arms 20 in more detail. FIG. 2 is a perspective view of a portion of the device with certain external components not illustrated in order to improve visibility. The device can have a suture arm driver 23, to which the suture arms 20 can rotatably attach at a first end thereof. The suture arms can be free at a second end opposite the first end, allowing the second end to swing outward such that the arms can move from the retracted position to the extended position, or to swing inward such that the arms can move from the extended position to the retracted position.

As illustrated, the suture arms 20 can rotate about a proximal end of the suture arm. In some embodiments, the suture arms can slide or move in other ways from the retracted to the extended position, or from the extended to the retracted position. In the illustrated embodiment, as the suture arms 20 rotate from the extended to the retracted position, the suture clasps 22 will move toward a distal end of the suturing device. In some embodiments, the suture arms can be configured such that the suture clasp moves distally as the arms rotate from the retracted to the extended position. In some embodiments, the suture arms can rotate about a distal end of the suture arm.

In some embodiments, as illustrated in FIG. 2, the suture arm driver 23 can translate along a central shaft 80. As it translates it can move the suture arms 20 with it. In some embodiments, the suture arm driver can translate far enough such that the suture arms can contact a section 81 of the elongate body 3, as illustrated. In some embodiments, the section 81 of the elongate body contacted by the suture arms can be angled. The ends of the suture arms opposite the suture arm driver can also have an angled surface 21, and as the suture arm driver moves farther toward the section 81 the suture arms 20 will be pushed outward toward the extended position. To move the arms from the extended position to the retracted position, the suture arm driver 23 can translate along the central shaft 80 in the opposite direction, and the suture arms 20 can return to the retracted position.

FIG. 3 is a perspective view of a section of the distal assembly 2 with certain external components not illustrated in order to improve visibility. FIG. 3 illustrates one embodiment of the suture arms 20 in an extended position. In some embodiments, the suture arms 20 can be generally straight. In some embodiments, the suture arms 20 can extend from the elongate body at approximately 90 degrees. In some embodiments, the suture arms can extend from the elongate body at an angle less than 90 degrees or greater than 90 degrees. In some embodiments, the suture arms can have angled or curved segments, and can extend from the elongate body at a first angle and have other sections at other angles relative to the elongate body. In some embodiments, the suture clasps 22 can be on a section of the suture arms that is at an angle relative to the elongate body that is different from the first angle.

With continued reference to FIGS. 2 and 3, in some embodiments the suture arms 20 can each have a bumper 28. The bumpers can be positioned such that they provide clearance for the suture arms to rotate to or from the extended position. Preferably, the bumpers 28 have a curved surface, but in some embodiments they can have flat sections. In some embodiments, the suture clasps 22 can have a beveled or tapered section 122 that is configured to receive a needle. The taper can help guide the needles into the suture clasps and toward a suture portion within a clasp. This can be beneficial if a needle has prolapsed slightly or otherwise deviated from a preferred alignment, such as an alignment with the center of a suture clasp 22.

Figure 4:
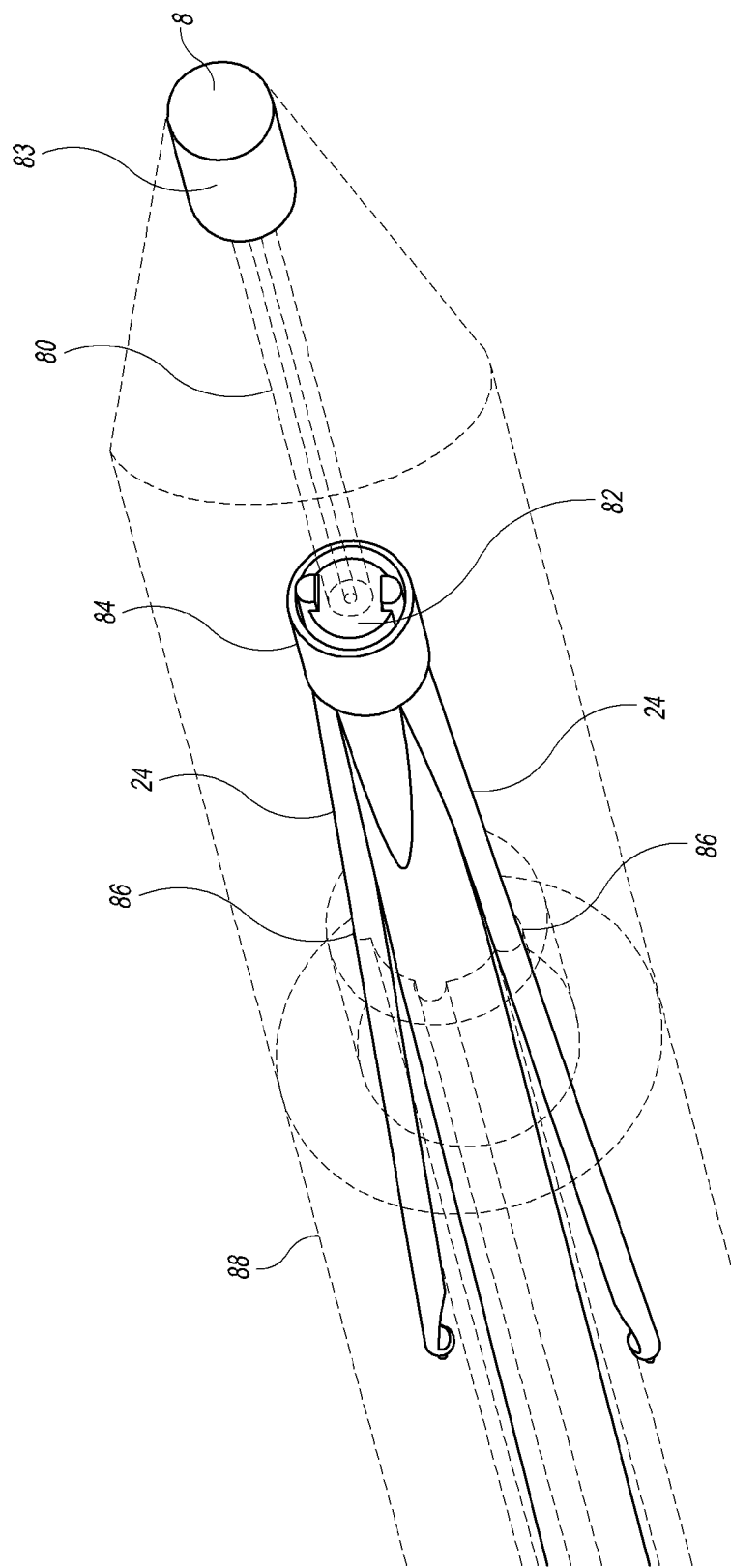
FIG. 4 is a perspective view of a portion of a suture device showing needles, and with certain external components not illustrated.

FIG. 4 is a perspective view of a section of the distal assembly 2 with certain external components not illustrated or made transparent in order to improve visibility. FIG. 4 illustrates two needles 24 instead of four for clarity, but as discussed above, in various embodiments the device can have a different number of needles. The needles are preferably located distal to the suture arms 20 and preferably point proximally toward the suture arms. In some embodiments, the needles can be located proximal to the suture arms and point distally toward the suture arms. The needles 24 can attach to a needle drive tube 82, which can be positioned around the central shaft 80 and which can translate along the central shaft. In some embodiments, as illustrated, a collar 84 can be used to lock the needles 24 to the needle drive tube 82.

Figure 5:
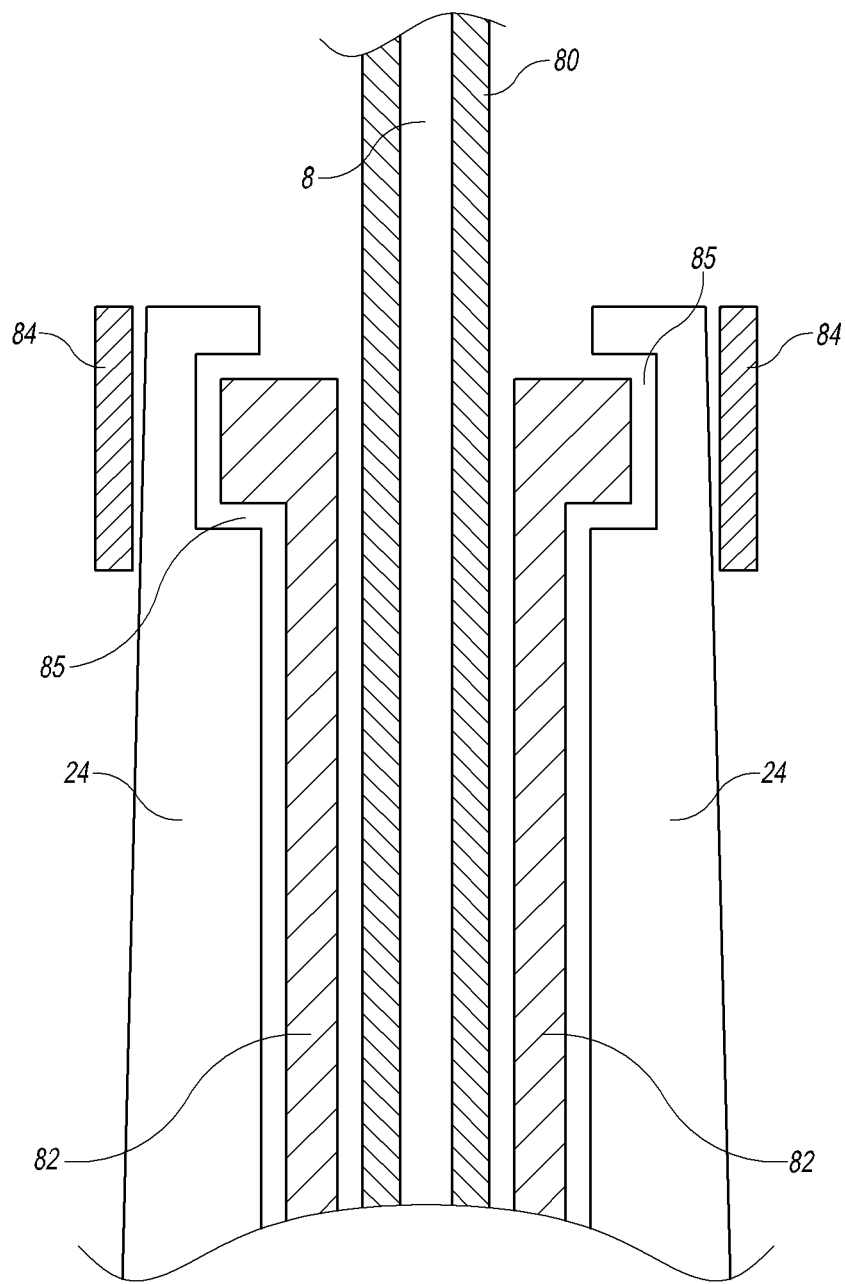
FIG. 5 is a cross sectional view of a portion of a suturing device used to lock needles to a drive tube.

FIG. 5 illustrates a cross sectional view of one embodiment where a collar 84 is used to lock the needles 24 to the needle drive tube 82. The needles 24 can have a notch 85 adjacent one end, and the needle drive tube 82 can have a corresponding protrusion that can slot into the notch. The collar 84 can surround both the needles and the needle drive tube, locking them into their respective positions. In some embodiments, as illustrated, the needle drive tube 82 can be narrower where it receives the collar than in other locations of the needle drive tube. This can help seat the collar so that it does not slide further along the needle drive tube. In some embodiments, the needles can attach to the needle drive tube without a collar. Also visible in FIG. 5 is the central shaft 80 with a guide wire lumen 8.

Returning to FIG. 4, when the needles 24 and needle drive tube 82 translate along the central shaft 80, they can also translate relative to an outer body 88. In some embodiments, the outer body 88 can have channels 86 that can guide the needles within the outer body. The channels can help direct the needles and can also provide a measure of support to the needles to prevent them from prolapsing or buckling. In some embodiments, each needle can fit entirely within a respective channel. In some embodiments, each needle can fit partially or at least partially within a respective channel. Also visible in FIG. 4 is a distal sleeve 83, present in some embodiments, which can help channel a guide wire into the central shaft 80.

The needle drive tube 82 can move the needles toward or away from the suture arms 20. As the drive tube moves the needles toward the suture arms 20 the needles will eventually reach the needle exit channels 26 (visible in FIG. 1B). The needle exit channels can be angled to direct the needles toward the suture arms 20, and specifically the suture clasps 22.

Figure 6:
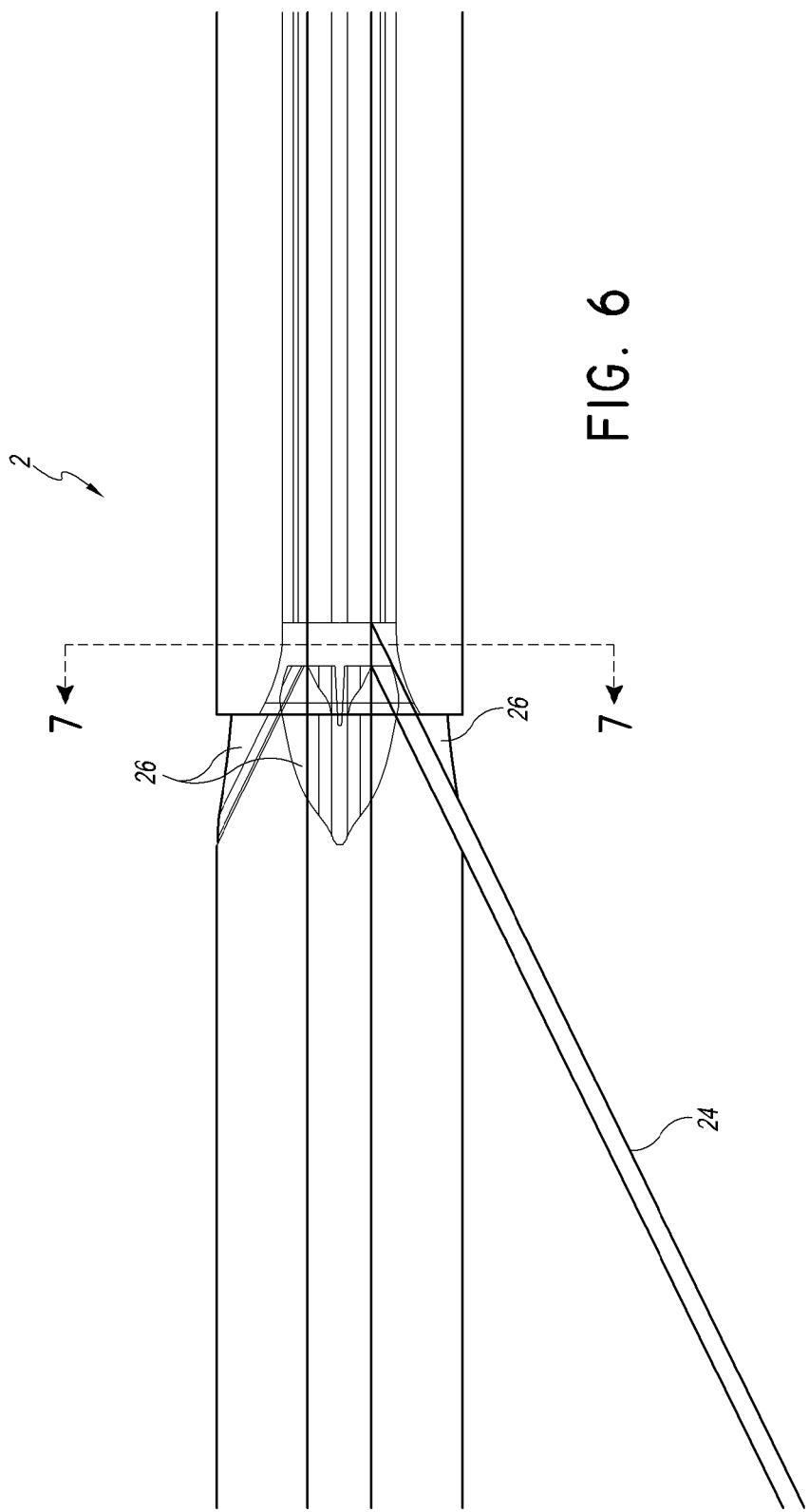
FIG. 6 is a transparent view of a portion of the distal assembly.
Figure 7:
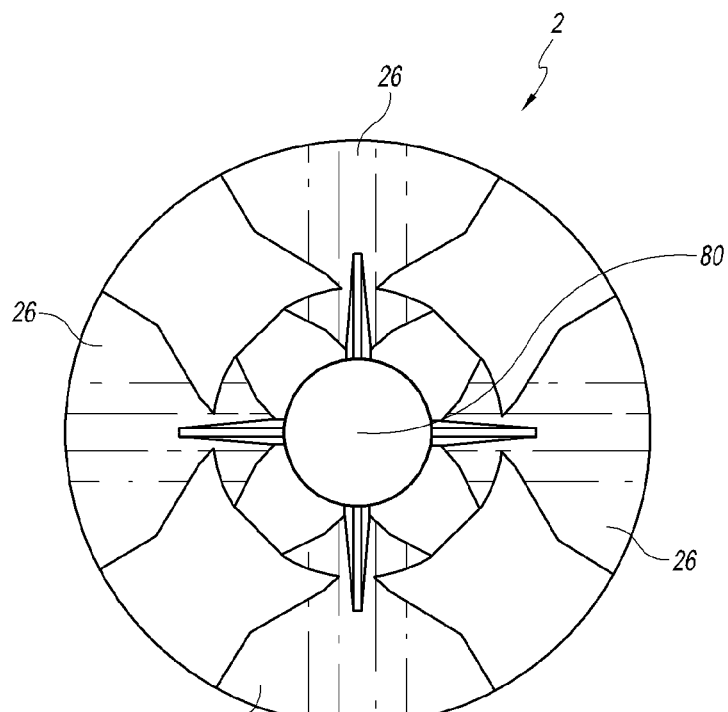
FIG. 7 is a cross sectional view of a distal assembly taken along the line 7-7 of FIG. 6.

FIG. 6 is a transparent view of a portion of the distal assembly 2 when the needle drive tube (not visible in this figure) has moved the needles 24 through the needle exit channels 26 and out of the distal assembly. Only one needle is illustrated in FIG. 6 so that the shape of the needle exit channels 26 can be more easily seen, but the illustrated embodiment would have four needles. FIG. 7 illustrates a sectional view of the distal assembly 2, taken along the line 7-7 visible in FIG. 6. As illustrated in FIG. 7, in some embodiments the needle exit channels 26 can extend radially outward along a line that passes through the longitudinal axis of the distal assembly. When a needle 24 is in a deployed position passing into a corresponding suture arm 20 and suture mount 22, at least the portion of the needle external to the distal assembly can form a plane with the corresponding suture arm 20. In some embodiments, the longitudinal axis of the distal assembly can lie on the plane formed by the needle and the corresponding suture arm. In some embodiments, the plane formed by at least the portion of the needle 24 external to the distal assembly 2 and the corresponding suture arm 20 can be parallel to and offset from the longitudinal axis of the distal assembly. In some embodiments, the longitudinal axis of the distal assembly can be angled relative to the plane formed by the needle and the corresponding suture arm.

Figure 8:
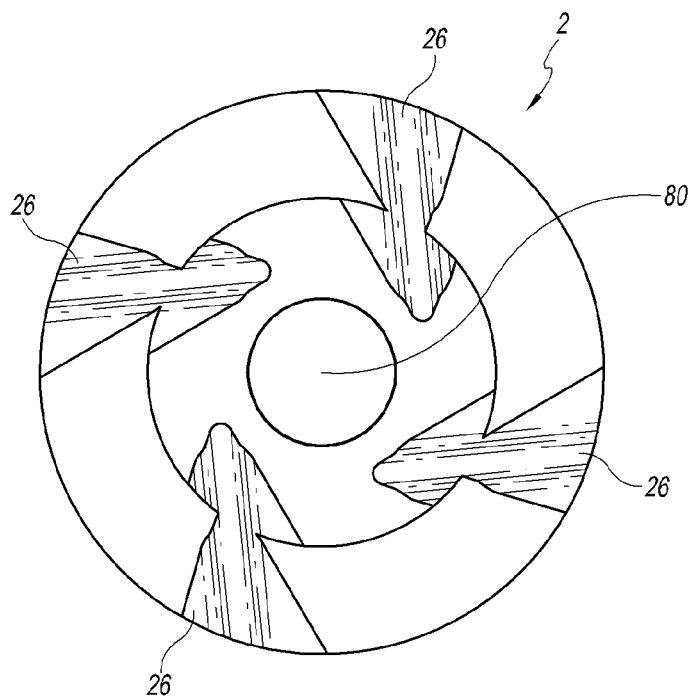
FIG. 8 is a cross sectional view of one embodiment of a distal assembly.

FIG. 8 illustrates a cross-sectional view, similar to the view of FIG. 7, of one embodiment of a distal assembly 2 with needle exit channels 26 that do not extend radially outward along a line that passes through the longitudinal axis of the distal assembly. Rather, the exit channels 26 can each have a longitudinal axis that is offset from a longitudinal axis of the distal assembly 2. This arrangement can be used with embodiments in which the longitudinal axis of the distal assembly is either parallel to and offset from the plane formed by a needle and corresponding suture arm, as described above, or is angled relative to the plane.

Figure 9A:
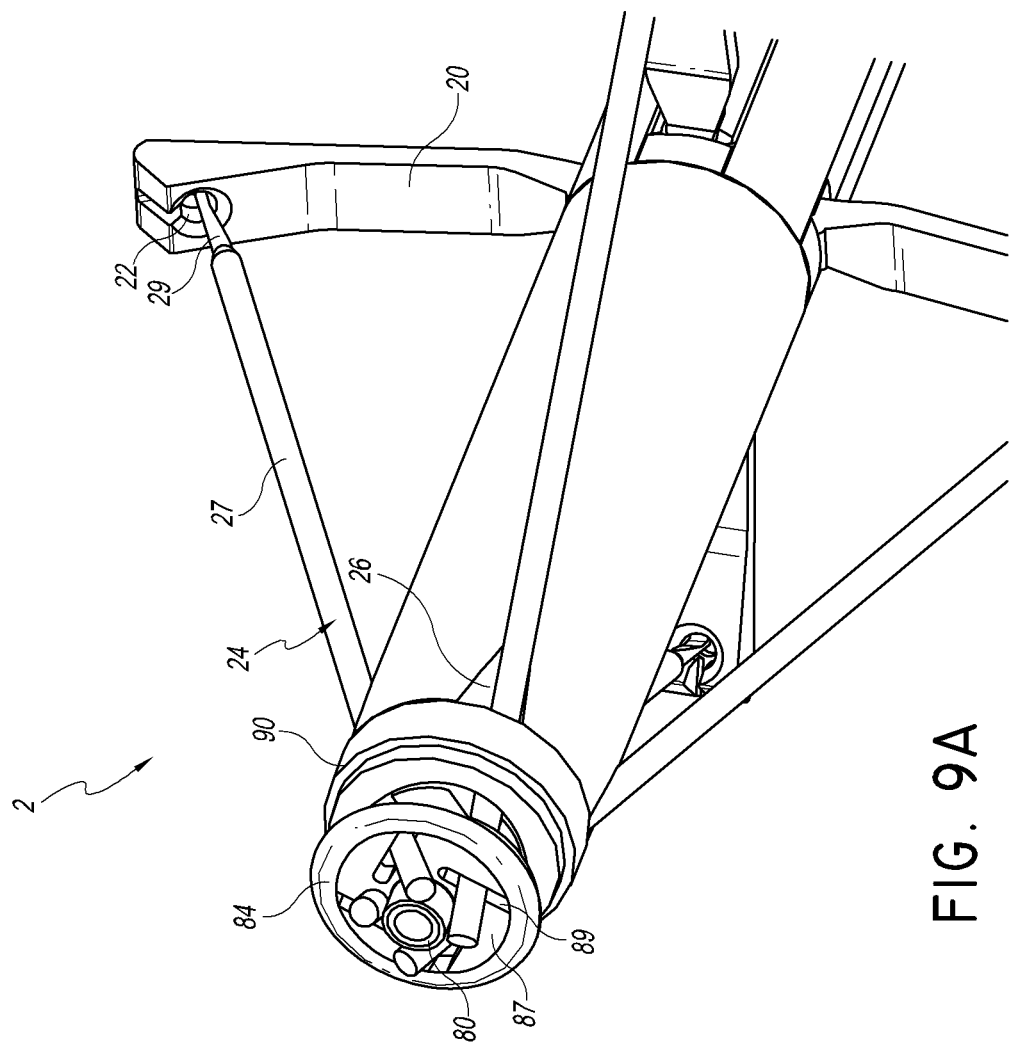
FIG. 9A is a perspective view of a section of one embodiment of a distal assembly.
Figure 9B:
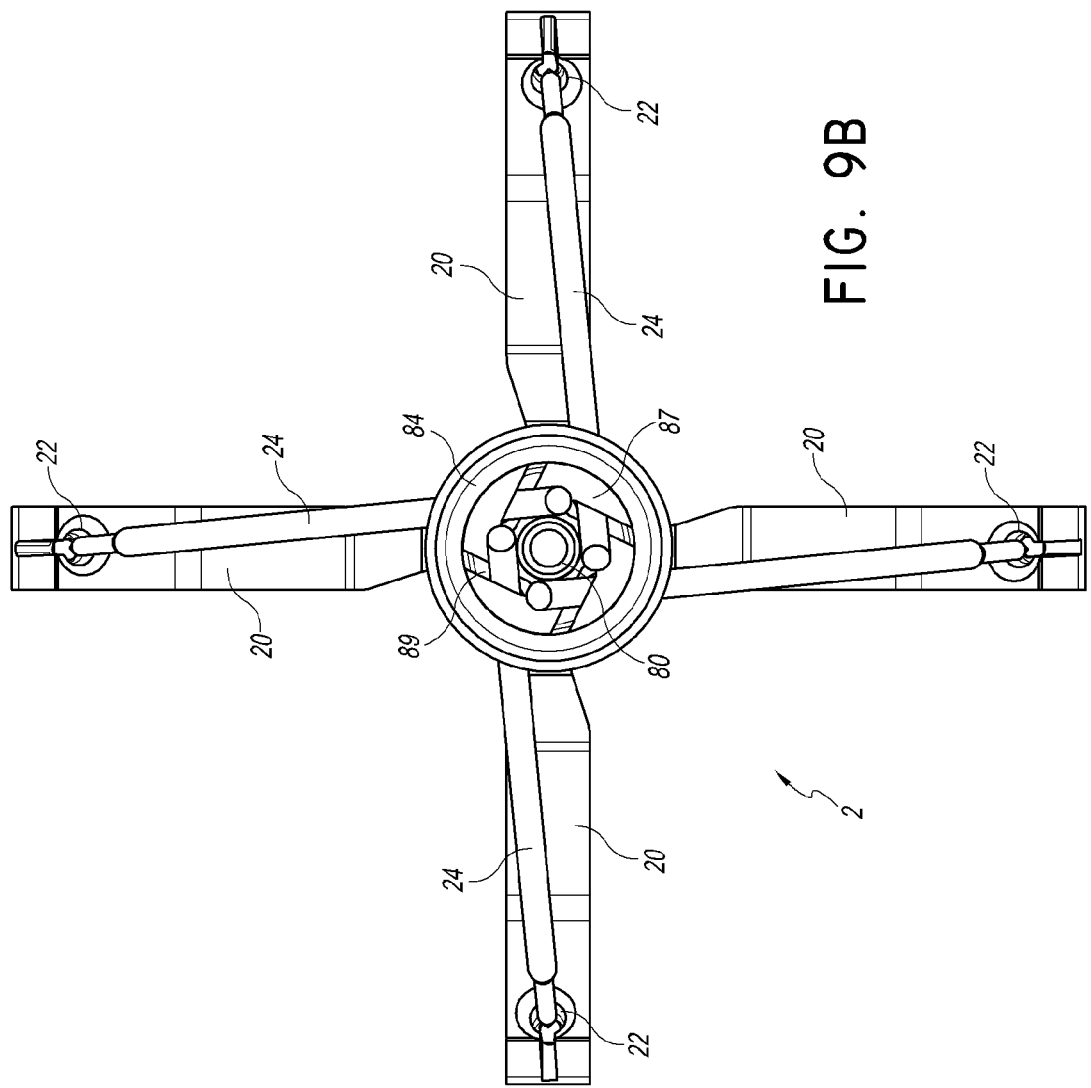
FIG. 9B is a top view of the second of FIG. 9A.

FIGS. 9A and 9B illustrate one embodiment in which the longitudinal axis of the distal assembly is angled relative to the plane formed by at least the portion of a needle 24 external to the distal assembly 2 and the corresponding suture arm 20. FIG. 9A is a perspective view of a section of the distal assembly with various components removed for visibility. FIG. 9B is a top view of the section shown in FIG. 9A. As illustrated, the needle exit channels 26 can be arranged as in FIG. 8, and the suture arms 20 can extend radially outward along a line passing through the longitudinal axis of the distal assembly. As illustrated in FIG. 9A, the needle exit channels 26 are spaced or offset from a plane defined by an extended suture arm and the longitudinal axis of the distal assembly, so that the needle 24 extends at an angle to this plane and intersects the plane at suture mount 22. As above, in some embodiments the suture arms can be symmetrically spaced about the distal assembly 2. In embodiments with four suture arms, as illustrated, they can be spaced 90 degrees apart from each other when extended.

In some embodiments, the suture arms can each have a longitudinal axis offset from the longitudinal axis of the distal assembly. In some embodiments, the offset for the suture arms can be the same as the offset for the needles, and the plane formed by a needle and corresponding suture arm can be parallel to and offset from the longitudinal axis of the distal assembly. In some embodiments, the needle exit channels can be arranged as in FIG. 7, the suture arms can each have a longitudinal axis offset from the longitudinal axis of the distal assembly, and the longitudinal axis of the distal assembly can be angled relative to the plane formed by a needle and corresponding suture arm.

In some embodiments, the needles 24 can attach to a mounting plate 87 positioned around a central shaft 80 of the distal assembly. The mounting plate can have one or more cutouts 89. In some embodiments, each needle can have a notch, as described above, and the needles can be positioned such that a notch interfaces with a cutout 89. This can at least partially lock the needles in place, allowing relative movement between each needle and the mounting plate only along the length of the cutout in which the needle is positioned. In some embodiments, a retaining ring or collar 84 can be positioned around the plate to lock the needles into position within the cutouts. In some embodiments, cutouts can be sized to substantially prevent any needle movement.

FIG. 9A illustrates the needles 24 in a deployed position in which a distal tip of each needle is within a suture mount 22. The mounting plate 87 can be configured to move along the length of the distal assembly, moving the needles with it. For example, the mounting plate can move away from the suture arms 20, pulling the needles 24 with it. In some embodiments, moving away from the suture arms can be in the distal direction. In some embodiments, moving away from the suture arms can be in the proximal direction. When the mounting plate moves far enough, the needles can move to a retracted position in which they are entirely or substantially within the elongate body.

In some embodiments, needles 24 can have different configurations that can help prevent prolapse or buckling. For example, as illustrated in FIG. 9A, in some embodiments a needle 24 can include a first, proximal section 27 with a first diameter and a second, distal section 29 with a second diameter. In some embodiments, the second diameter can be sized for insertion into a suture clasp to receive a suture end. In some embodiments, the first diameter can be greater than the second diameter. The greater first diameter can help improve resistance of the needle to prolapse, buckling, or any other undesired movements. In some embodiments, the needle can transition from the first section to the second section between a needle exit channel 26 and a suture clasp 22.

Methods of Use

The suturing device can have a guide wire lumen, not illustrated, that can allow the suturing device to follow a guide wire 6 into a position within the heart. In a typical procedure, a hollow needle (delivered, for example, through a trocar into the thoracic cavity) can be used to puncture an opening at or near the apex of the heart and to feed a guide wire through the opening and into the heart. The suturing device can then follow the guide wire into the opening and into the heart. The suturing device can have a tapered end at the distal end of the elongate body 3, as illustrated in FIG. 2, and the taper can be configured such that the device is capable of following the guide wire through the opening formed by the needle, widening the opening as the device is advanced further into the heart. The device can then be used to place a plurality of sutures through the tissue of the heart near the opening, while maintaining or nearly maintaining haemostasis, as described below. The device can then be removed, leaving the sutures in place and the first sheath within the opening in the heart, thereby allowing other devices to be inserted through the sheath to perform a desired procedure within the heart. The sutures can then be used to tighten the opening closed after the desired procedure has been performed and while the sheath and/or device is being removed.

Figure 10:
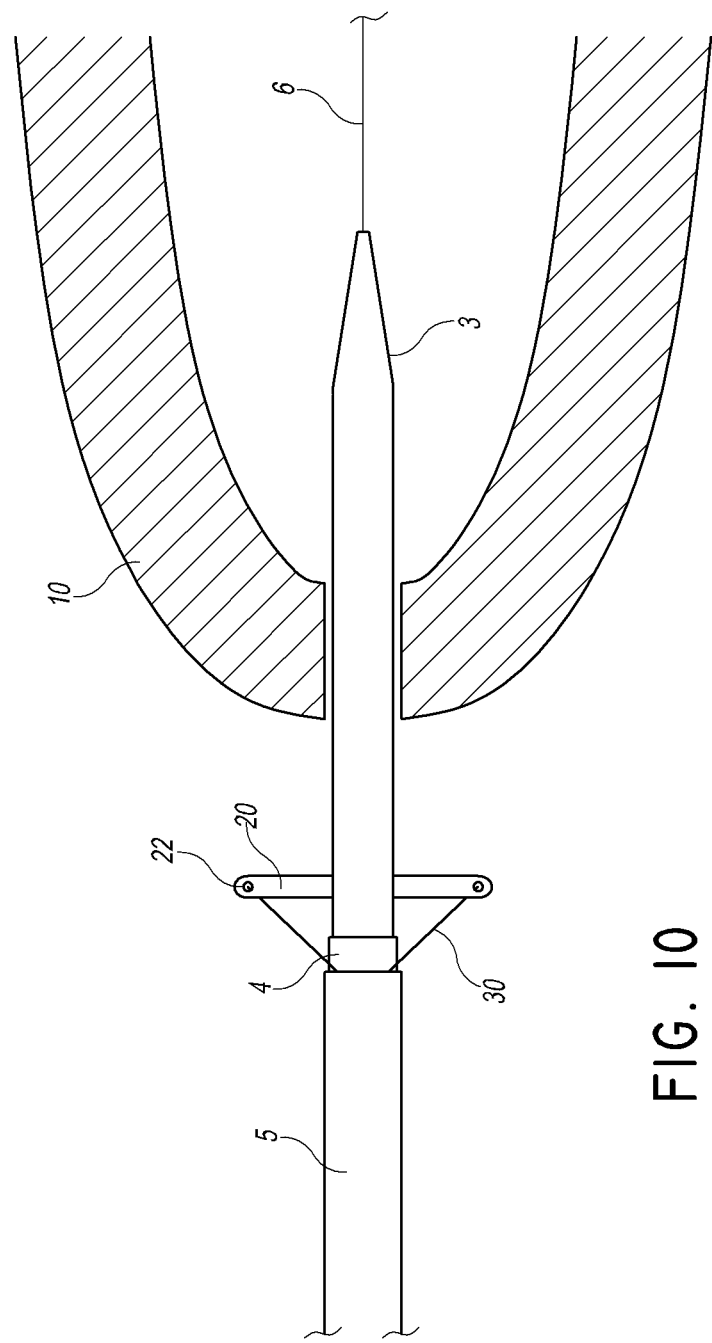
FIG. 10 is a cross sectional schematic representation of the device of FIG. 1 passing through an opening at the apex of a heart.

FIGS. 10-19 illustrate one method of using the suturing device 1 to place sutures through tissue near an opening in the heart and to position a sheath through the opening to allow for entry of other devices, while maintaining or nearly maintaining haemostasis. As discussed above, the device 1 can follow a guide wire 6 through a puncture in or near the apex of a heart, the tapered end of the device widening the opening in the heart wall 10, as the device enters further into the heart. The suture arms 20 can be moved into an extended position, as illustrated in FIG. 10, which is a view of the device of FIG. 1 as it enters a heart. FIGS. 10-19 show a cross sectional view of the heart, and only show the two arms 20 of the device that lie in the illustrated planes. Although the method illustrated in FIGS. 10-19 can be performed with a device having only the two illustrated arms, the description of the method will be with reference to the device of FIG. 1, which has four arms. Each suture arm 20 holds a separate suture 30, so there are a total of four separate sutures when the device is positioned as in FIG. 10.

Figure 11:
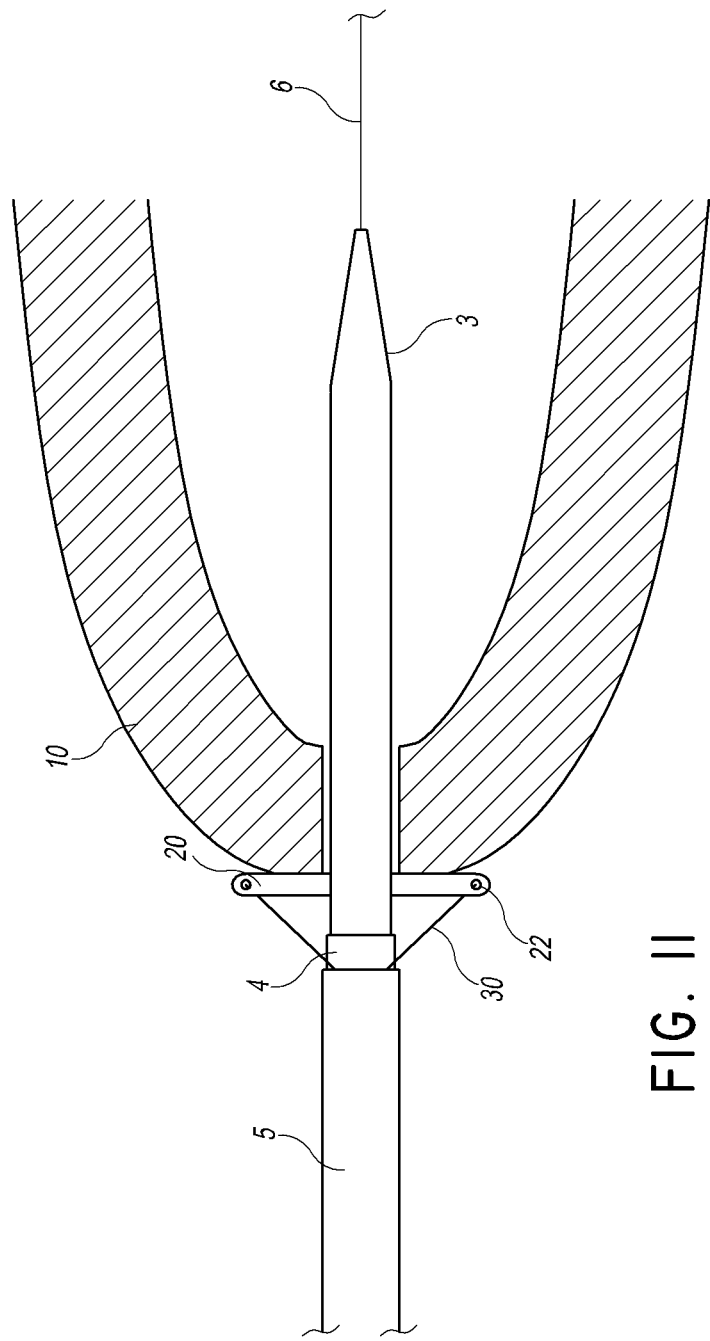
FIG. 11 is a schematic representation as in FIG. 10 showing arms of the device in contact with the heart.
Figure 12:
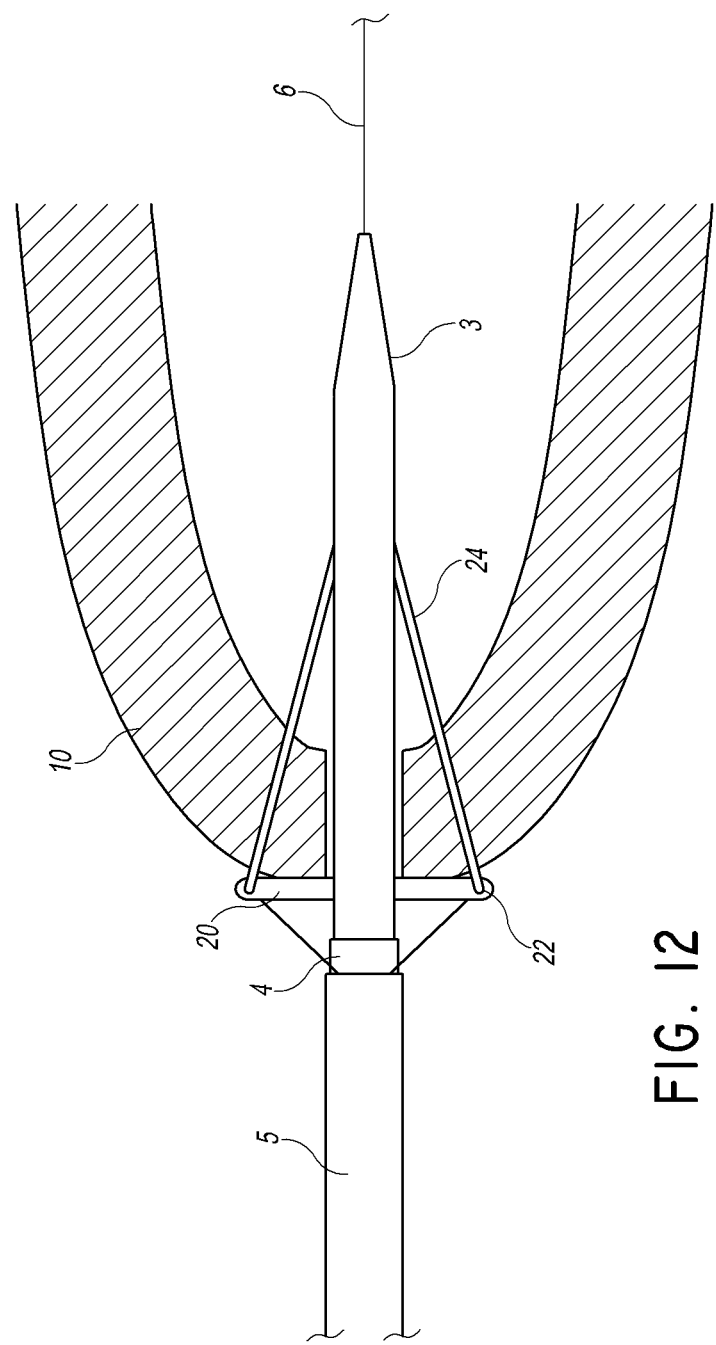
FIG. 12 is a schematic representation as in FIG. 11 showing suture catch mechanisms engaging suture clasps.
Figure 13:
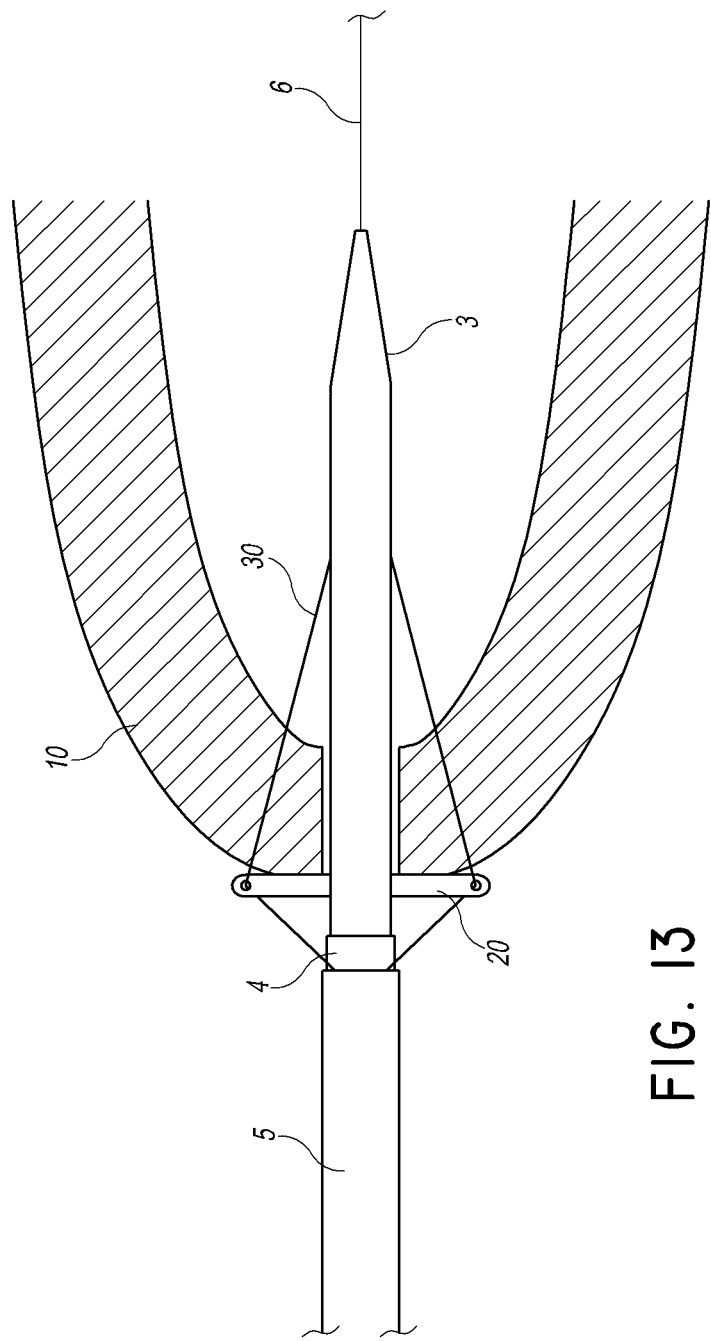
FIG. 13 is a schematic representation as in FIG. 12 showing the suture catch mechanisms retracted into the device and suture portions extending through the heart wall.

With the suture arms in the extended position, the device can be further advanced into the heart until the suture arms press against tissue of the heart, as illustrated in FIG. 11. Once in position at the base of the heart, needles 24 can fire and extend from a distal end of the elongate body 3, through tissue of the heart, and into the suture clasps 22, as illustrated in FIG. 12. In some embodiments, the device can have a needle 24 that corresponds to each suture arm, a needle that corresponds to multiple suture arms, or multiple needles that correspond to a single suture arm. The needles can engage the sutures 30, releasably positioned in the suture clasp, such that when the needles retract back into the elongate body they draw a portion of suture with them, as illustrated in FIG. 13. In some embodiments, the needles can fire simultaneously, and in some embodiments they can fire sequentially.

Figure 14:
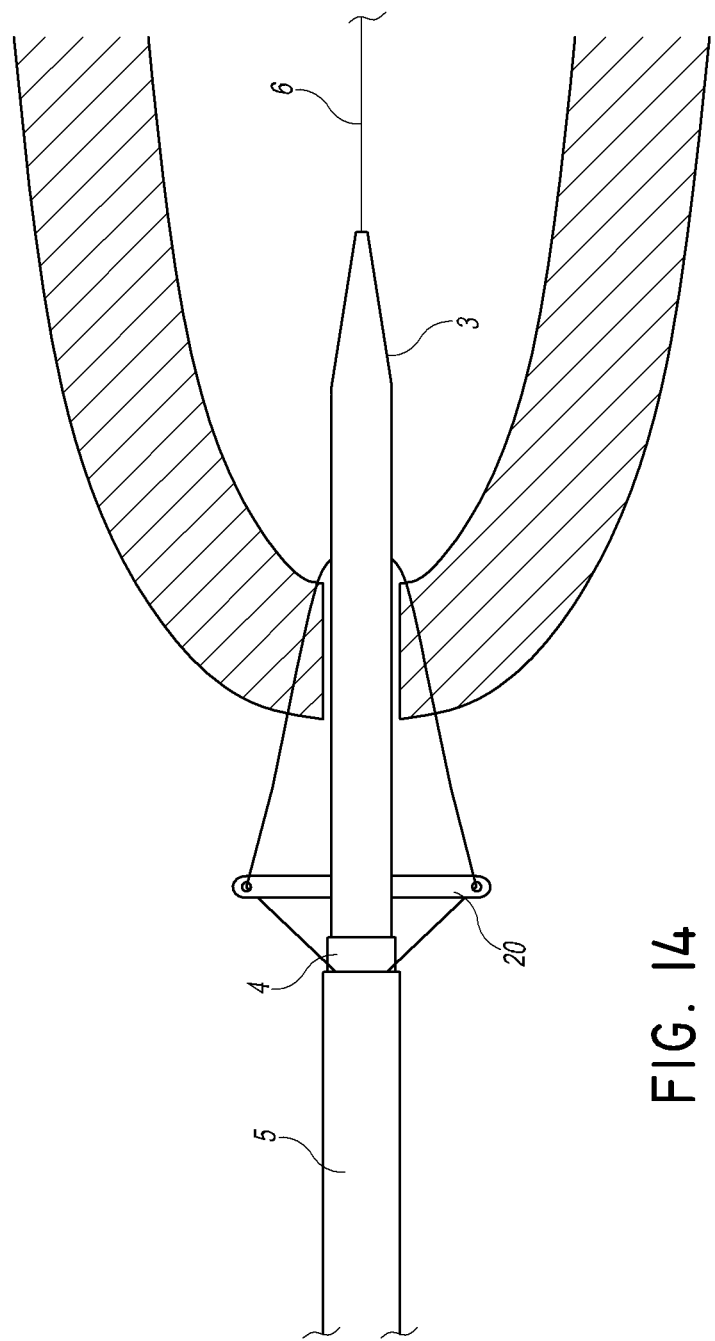
FIG. 14 is a schematic representation as in FIG. 13 showing the device partially withdrawn from the heart.
Figure 15:
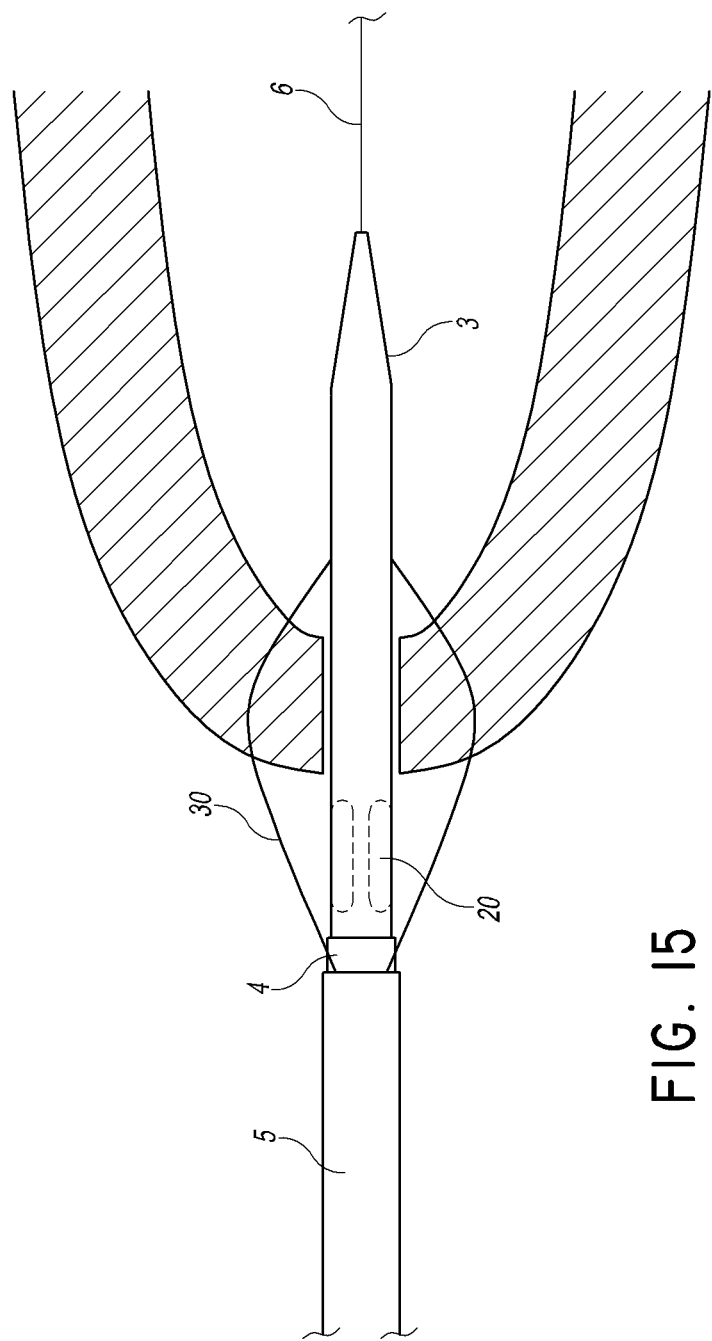
FIG. 15 is a schematic representation as in FIG. 14 showing arms of the device in a retracted position.
Figure 16:
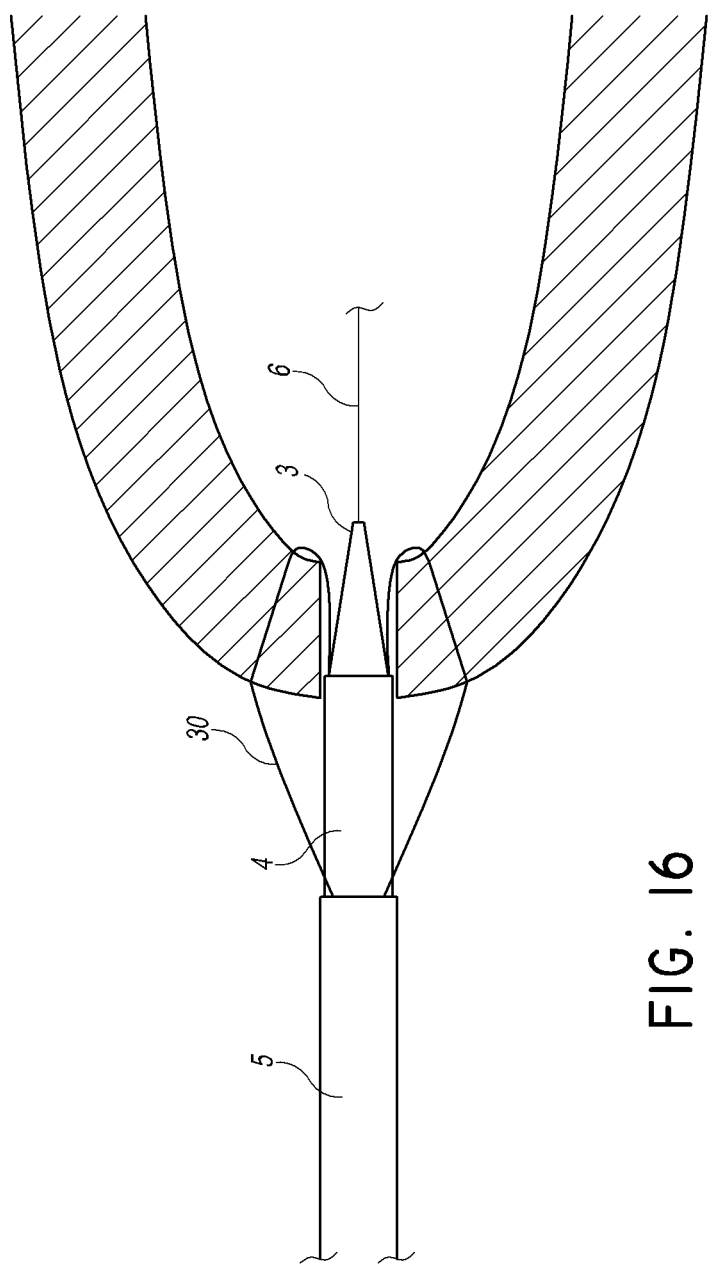
FIG. 16 is a schematic representation as in FIG. 15 showing a first sheath advancing and the device withdrawing from the heart.

Once the needles have fired and drawn sutures through tissue of the heart, the device can be withdrawn slightly from the heart in order to allow the suture arms to return to a retracted position, as illustrated in FIG. 14. In embodiments where the distal ends of the suture arms move proximally as the suture arms rotate from an extended to a retracted position, it may not be necessary to withdraw the device prior to retracting the suture arms. Once the suture arms have been retracted, as illustrated in FIG. 15, the sutures 30 will run from within the device, through the tissue of the heart, and to a proximal end of the device while passing beneath the second sheath 5 but over the first sheath 4, as illustrated in FIG. 15. The first sheath 4 can then be moved into the opening in the heart while the elongate body 3 is withdrawn, as illustrated in FIG. 16. In some embodiments, the sheath can fully pass into the opening before the elongate body has begun to be withdrawn. In some embodiments, the elongate body can begin to be withdrawn before the sheath has entered the opening of the heart. Regardless of the order in which the motions occur, in order to maintain haemostasis either the sheath or the elongate body are preferably at least partially within the opening of the heart during the procedure. In FIG. 16, the sheath has begun to be advanced into the opening of the heart while the elongate body has begun to be withdrawn.

Figure 17:
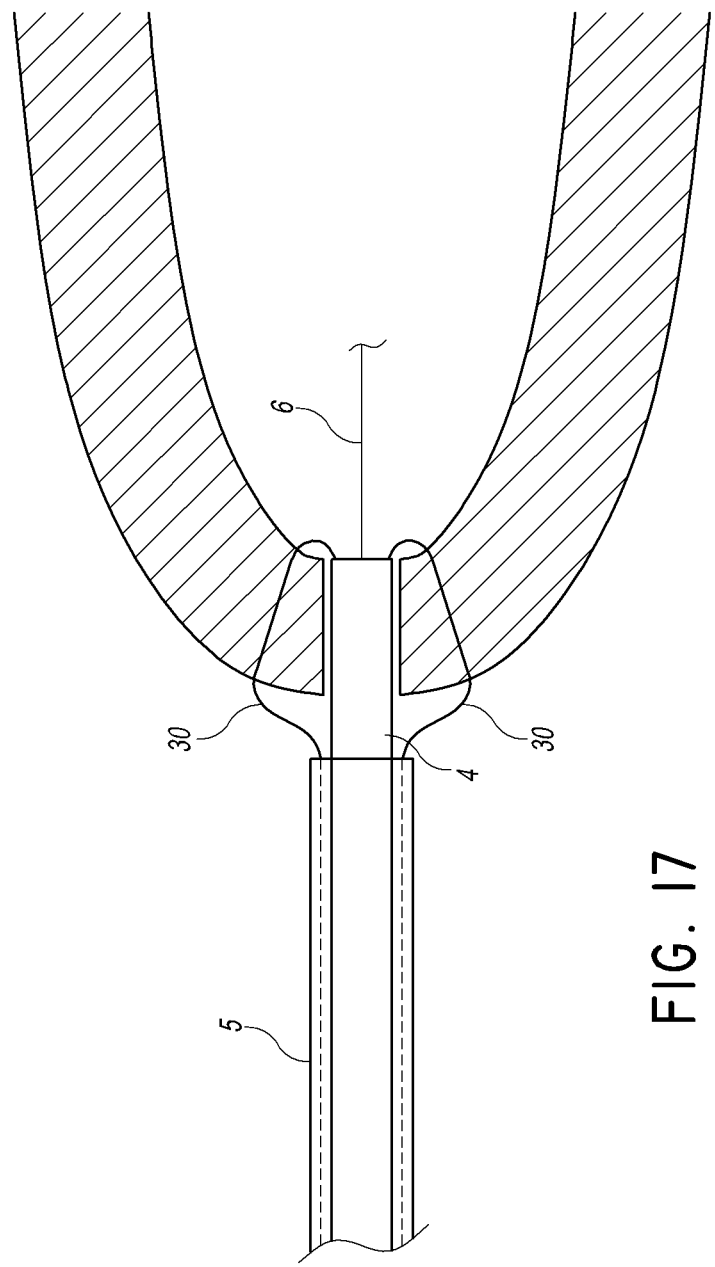
FIG. 17 is a schematic representation as in FIG. 16 showing the device withdrawn and the first sheath advanced into the heart wall.
Figure 18:
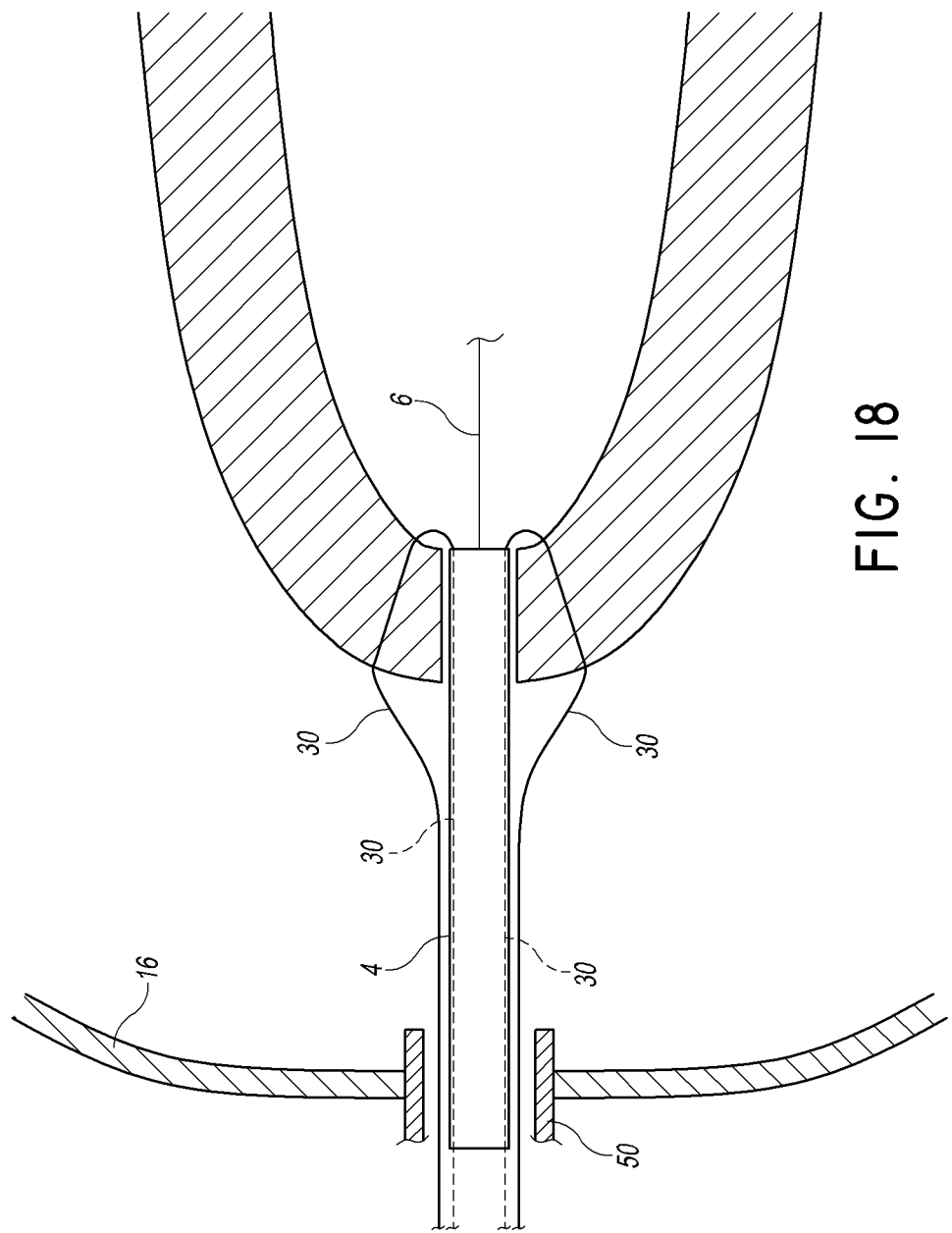
FIG. 18 is a schematic representation as in FIG. 17 showing suture ends passing through a trocar inserted into a chest wall.

In FIG. 17, the first sheath 4 has been fully advanced into the opening of the heart and the elongate body has been withdrawn. The first sheath 4 can have a hemostatic valve (not illustrated) that can prevent extraneous bleed back, and in some embodiments the valve can be at a proximal end of the first sheath 4. The suture ends that were within the elongate body now pass through the first sheath 4 and run to a proximal position outside of the patient where they can be manipulated, as illustrated in FIG. 18. From the proximal position of those suture ends, the sutures run through the sheath and into the heart, through tissue of the heart, and back to the proximal position while remaining outside of the first sheath 4 and inside of the second sheath 5. The second sheath 5 has been illustrated wider than in previous figures in order to improve visibility of sutures 30 running between the first and second sheaths. In some embodiments, the second sheath 5 can be wider or narrower in order to have a looser or tighter fit around the first sheath 4, and the first sheath can be wider or narrower in order to have a looser or tighter fit around the elongate body.

In FIG. 18, the second sheath 5 has been removed from around the first sheath 4 (e.g. by peeling it off), and the portions of the sutures 30 within the first sheath 4 are illustrated. FIG. 18 also illustrates the proximal end of the first sheath 4, which can be extending through a trocar 50 positioned through the chest wall 16. Each suture 30 has a free end at the proximal position outside of the patient that passes through the first sheath 4, into the heart, through tissue of the heart, and back to the proximal position while remaining outside of the first sheath 4. FIG. 18 only illustrates two separate sutures 30, but the illustrated embodiment has two more sutures 30 (for a total of four) that pass through heart tissue in a plane substantially perpendicular to the illustrated plane. Thus, there are four suture ends that pass through the first sheath 4 and four suture ends that pass outside of the first sheath 4. The four separate sutures are shown schematically in FIG. 22, discussed further below. The guide wire 6 also passes through the first sheath 4, but it is not shown within the first sheath in FIG. 18 for the sake of clarity.

Figure 19:
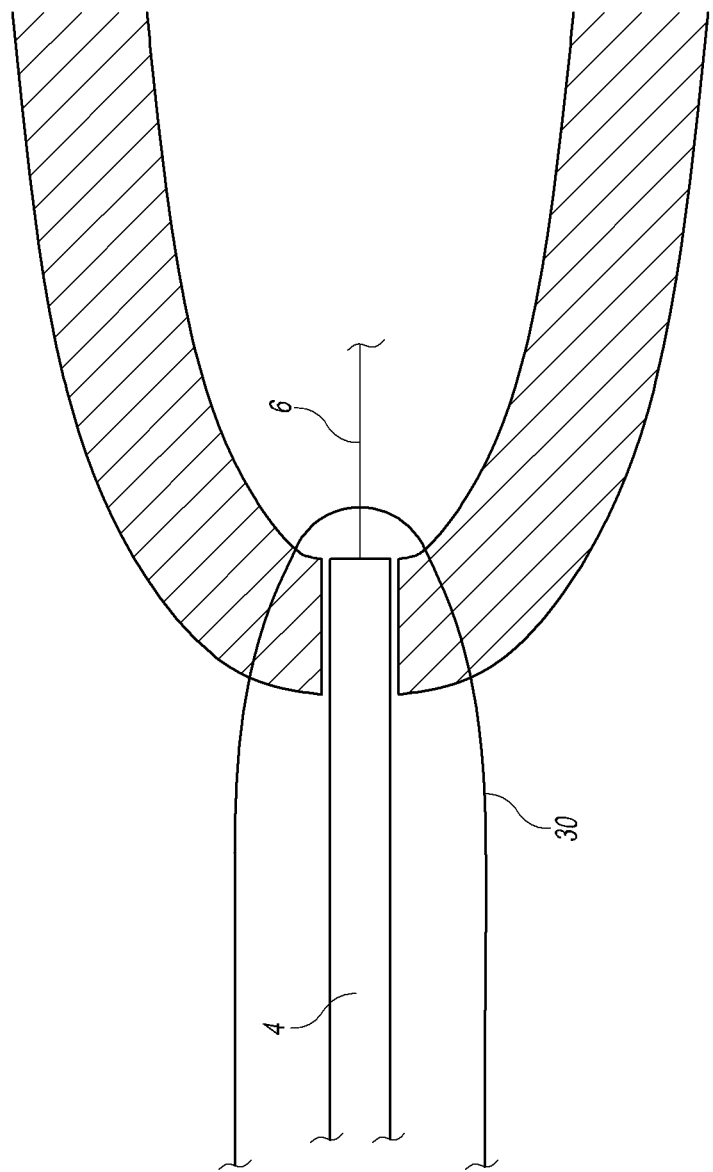
FIG. 19 is a schematic representation as in FIG. 18 showing a suture portion pulled into the heart.

Suture ends that pass through the first sheath 4 can be secured together with a knot or other device. Further details regarding a device for joining sutures are provided in U.S. Patent Application Publication No. 2011/0190793, published on Aug. 4, 2011, which is hereby incorporated by reference herein in its entirety. In some embodiments, suture ends that pass through the first sheath 4 can be secured together in pairs, each pair having suture ends that had been releasably attached to arms 20 spaced 180 degrees about the circumference of the elongate body 3 of the device 1. By then pulling on one or more of the remaining free suture ends, the joined suture 30 can be pulled through the first sheath 4 and into the heart, as illustrated in FIG. 19. FIG. 19 only shows one suture, but when the two pairs of suture ends that pass through the first sheath 4 have been secured together and pulled into the heart, a second suture would pass through the heart in the plane substantially perpendicular to the illustrated cross section.

In some embodiments, the point where a pair of suture ends has been joined together can be passed through the tissue of the heart and outside of the heart by pulling on one of the remaining free suture ends. In some embodiments, prior to joining the two suture ends that pass through the first sheath, a pledget can be slidably attached to a suture end, such as by threading a suture end through a hole in the pledget. After the two suture ends that pass through the first sheath have been secured together, the joined suture can be pulled through the tissue of the heart by one of the remaining free ends until the pledget contacts an inner surface of the heart wall, where it may remain. In some embodiments, prior to or after joining the two suture ends within the sheath, a pledget can be attached to a free suture end that passes outside of the first sheath 4. With the two suture ends within the first sheath joined, the opposite free suture end can be pulled until the pledget contacts an outer surface of the heart, where it may remain.

FIGS. 20A-24B illustrate various methods and embodiments of closing an opening within a heart, including the use and placement of pledgets. The methods and embodiments described herein can also be used to close openings in other biological structures. Thus, although the ends of sutures are variously referred to herein as passing through or outside of the first sheath, such descriptions can also refer respectively to suture ends that pass through or outside of an opening in a heart or other biological structure.

In some embodiments, it can be useful to use a threader 60 to attach a pledget to a suture. FIG. 20A illustrates one embodiment of a threader, which can have a handle 62 and a section extending from the handle 62 to form a collapsible loop 64 at one end. In some embodiments, the loop can be made of wire. The loop 64 can be fed through a pledget 70, as illustrated. Also as illustrated, the loop can be fed through the pledget in two locations, though in some embodiments it can be fed through only one or more than two locations. A free end of suture can then be fed through the loop and the loop can be pulled back through the pledget, bringing the suture with it. FIG. 20B illustrates a single suture 30 pulled through a pledget 70 in two locations. This can be done by arranging the threader and pledget as illustrated in FIG. 20A, or by using a threader to feed a suture through a first end of the pledget and then using the threader to feed the suture through the second end of the pledget.

In some embodiments, a threader 60 can have a first collapsible loop 64 and a second collapsible loop 66, as illustrated in FIG. 21A. In some embodiments, each loop can be passed through separate locations of a pledget 70, as illustrated. A separate suture can be fed through each loop and then pulled through the pledget, leading to the arrangement of FIG. 21B. In some embodiments, the arrangement of FIG. 21B can be achieved by using a threader with a single loop to separately pull a different suture through each end of the pledget. In some embodiments, a threader can have more than two collapsible loops.

Figure 22:
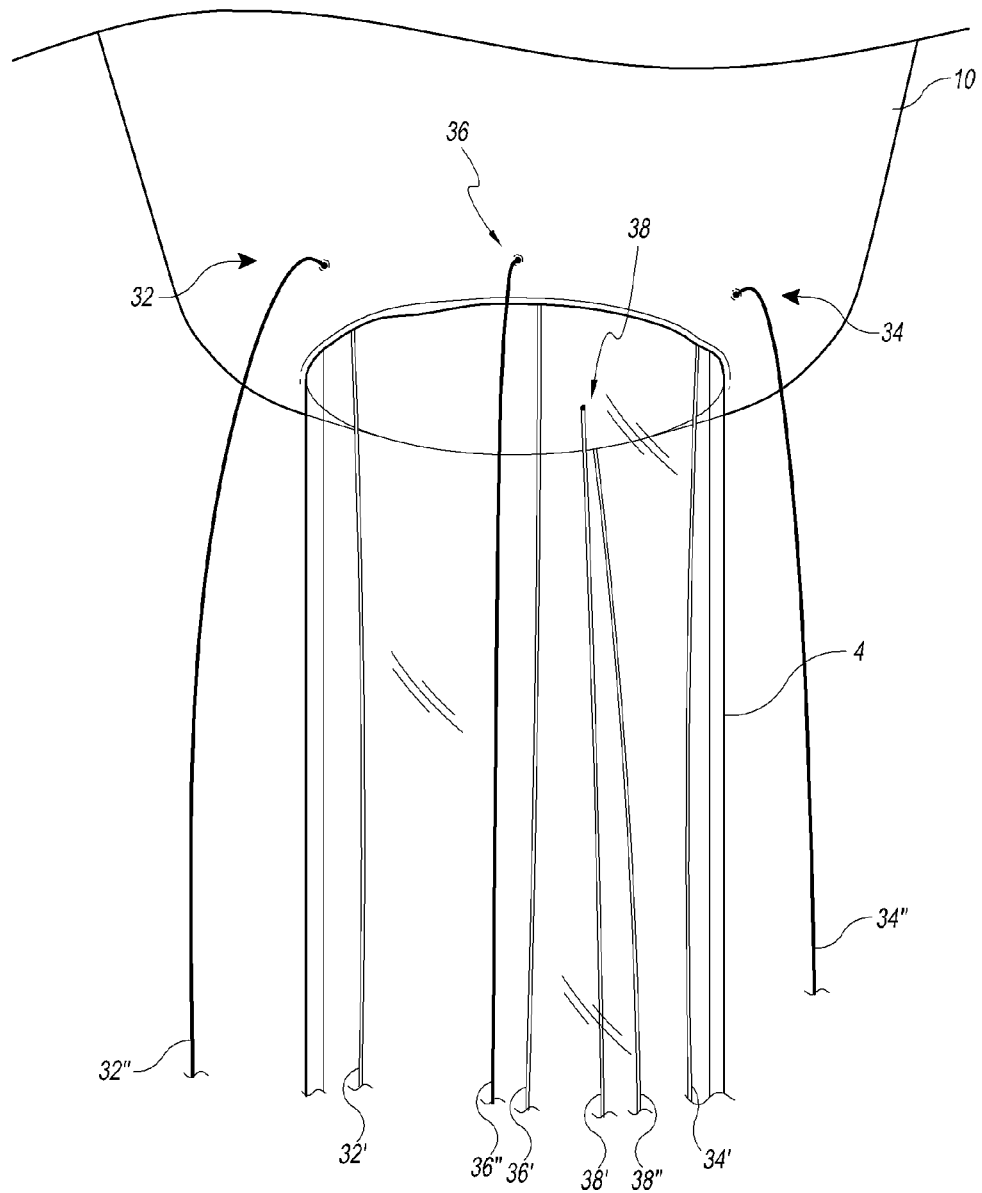
FIG. 22 is a schematic perspective view of a portion of a heart with four separate sutures running through heart tissue.

FIG. 22 illustrates a schematic of a perspective view of a portion of a heart in which a suturing device has inserted four separate sutures through the tissue of the heart wall 10. In some embodiments, this can be done with a suturing device that has four arms. As discussed above, a sheath, such as the first sheath 4, can be positioned at least partially within the opening in the heart. A length of suture corresponding to each arm of the device can pass from outside of the heart, through tissue of the heart, and then through the sheath. For example, as illustrated, a first suture 32, a second suture 34, a third suture 36, and a fourth suture 38 pass through the tissue of the heart. Each suture has a first end 32', 34', 36', 38' that passes through the sheath 4 and a respective second end 32", 34", 36", 38" that runs outside of the sheath. Pledgets can then be attached to various suture ends according to any method described above.

Figure 23A:
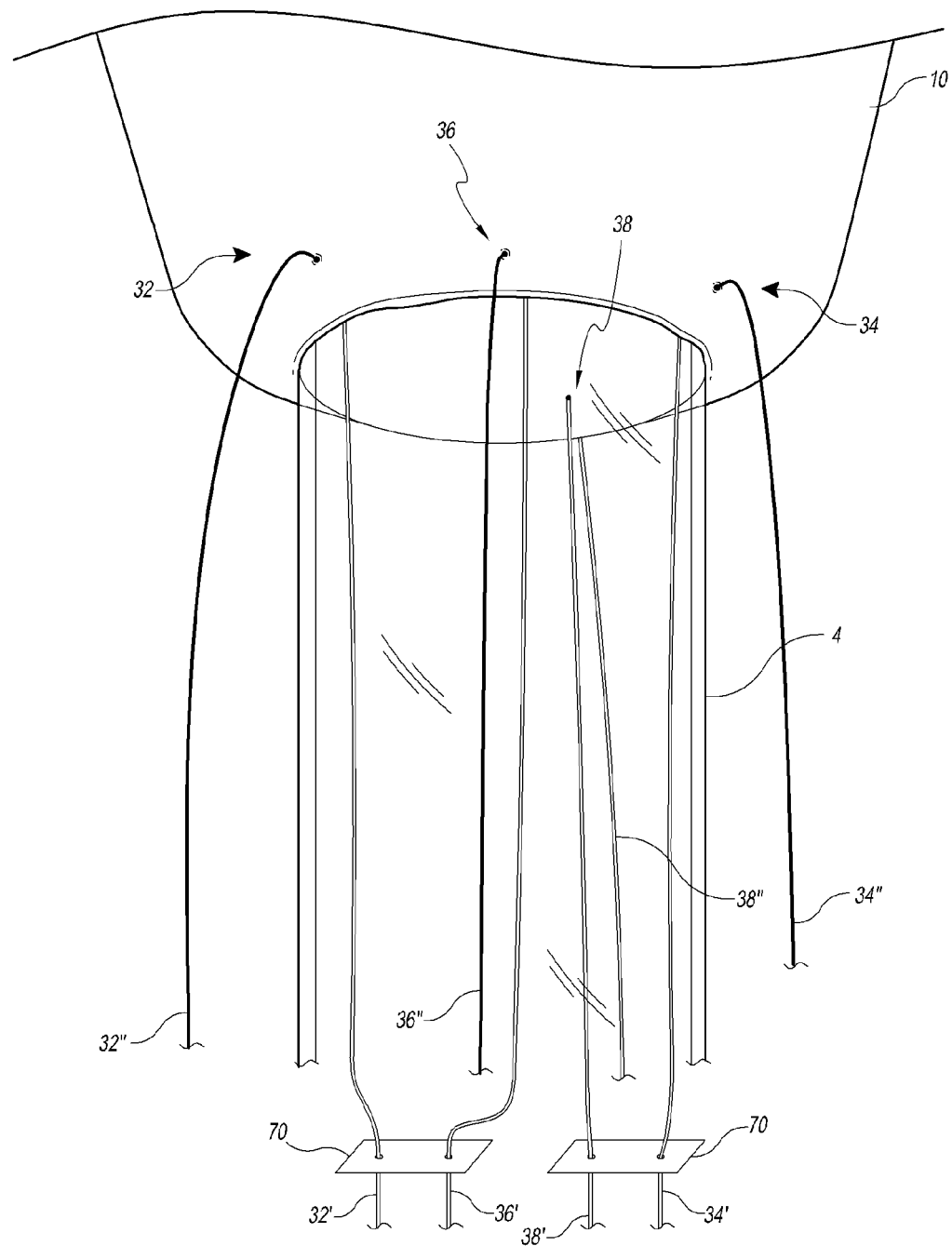
FIG. 23A is a schematic view of the portion of the heart of FIG. 22 with two pledgets attached to sutures according to one embodiment.
Figure 23B:
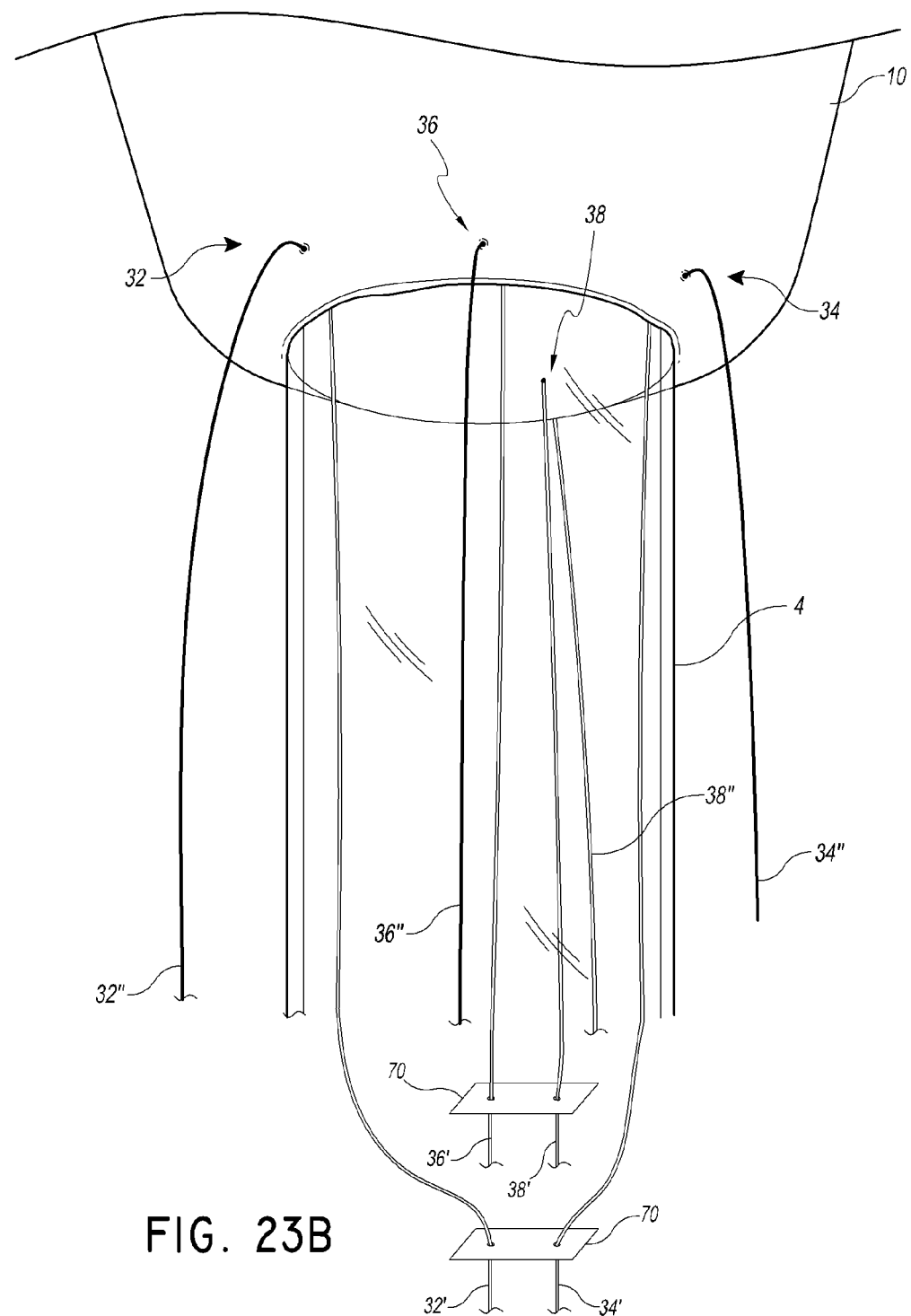
FIG. 23B is a schematic view of the portion of the heart of FIG. 22 with two pledgets attached to sutures according to one embodiment.

FIGS. 23A and 23B illustrate two ways in which pledgets (internal pledgets) can be attached to the first suture ends, each way yielding a different result when the pledgets are then pulled into the heart. FIG. 23A illustrates an embodiment where adjacent suture ends that run through the sheath 4 are fed through opposite ends of the same pledget 70. Thus, for example, the first end 32' of the first suture 32 can be fed through a first end of a pledget 70 while the first end 36' of the third suture 36 can be fed through a second end of the pledget 70. Similarly, the first end 34' of the second suture 34 can be fed through a first end of a second pledget 70 while the first end 38' of the fourth suture 38 can be fed through a second end of the second pledget 70.

FIG. 23B illustrates an embodiment where opposite suture ends that run through the sheath 4 are fed through opposite ends of the same pledget 70. Thus, for example, the first end 32' of the first suture 32 can be fed through a first end of a pledget 70 while the first end 34' of the second suture 34 can be fed through a second end of the pledget 70. Similarly, the first end 36' of the third suture 36 can be fed through a first end of a second pledget 70 while the first end 38' of the fourth suture 38 can be fed through a second end of the second pledget 70. In some embodiments, other arrangements of attaching suture ends to pledgets can be employed.

Once the sutures have been fed through the pledgets, opposing suture sections that pass through the first sheath can be secured together and pulled into the heart, as discussed with respect to FIG. 19. For example, suture ends 36' and 38' can be secured together to form a single suture, as can suture ends 32' and 34'. One or more of the suture ends 32", 34", 36", 38", which run outside of the sheath 4, can then be pulled until the pledgets are brought into the interior of the heart. After a procedure is performed within the heart and the sutures are tightened to close the opening in the heart, the pledgets 70 will form different arrangements depending on how they were originally placed on the sutures.

Figure 24A:
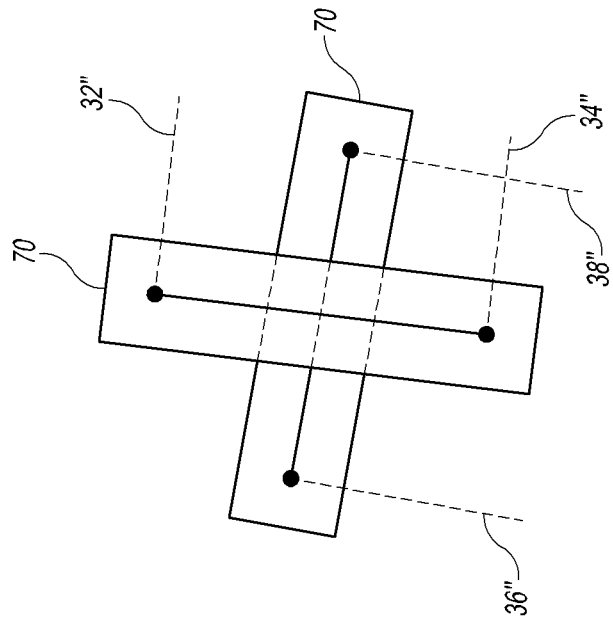
FIG. 24A is a schematic view of pledgets arranged according to the embodiment of FIG. 23A.
Figure 24B:
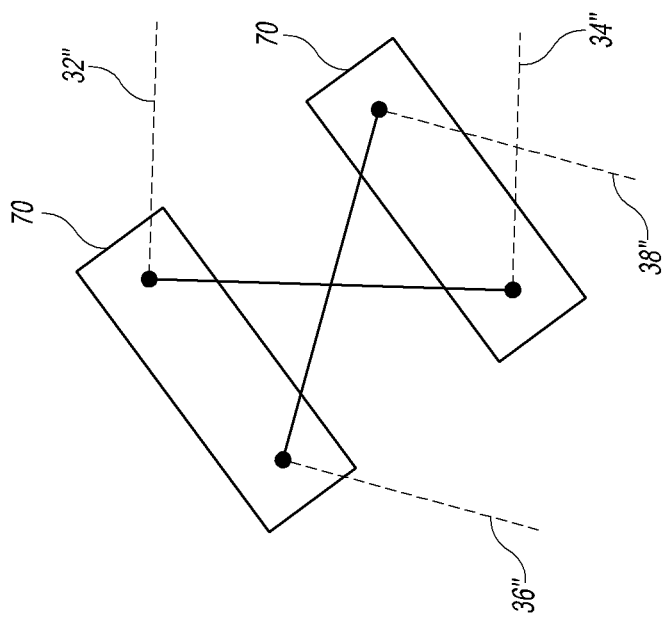
FIG. 24B is a schematic view of pledgets arranged according to the embodiment of FIG. 23B.

FIGS. 24A and 24B illustrate a schematic view from inside of the heart of two different pledget placements once the opening in the heart has been tightened. FIGS. 24A and 24B correspond to the pledget placement of FIGS. 23A and 23B, respectively. As can be seen, placing the pledgets according to the embodiment of FIG. 23A yields two adjacent pledgets 70. In some embodiments, the pledgets can partially overlap. The arrangement of FIG. 23B yields pledgets that cross each other, as illustrated in FIG. 24B.

In some embodiments, one or more pledgets (external pledgets) can be placed on the second suture ends 32", 34", 36", 38", which run outside of the sheath 4. The same placement techniques described above can be used. For example, suture ends that are located across from each other can be fed through opposite ends of a single pledget. In such embodiments, where four or more separate suture strands are used the pledgets can cross each other. Similarly, where adjacent suture ends are fed through opposite ends of a single pledget, the pledgets can be adjacent to each other.

The external pledgets are preferably placed on the sutures after the internal pledgets are placed on the first suture ends 32', 34', 36', 38'. In some embodiments, however, the external pledgets can be placed before the internal pledgets are placed. In some embodiments, the external pledgets can be placed even if no internal pledgets are placed. Once external pledgets are placed on the lengths of suture, they can be moved to a position adjacent heart tissue through a variety of methods. In some embodiments, external pledgets can be moved adjacent heart tissue by pulling a respective first suture end 32', 34', 36', 38' before first suture ends are secured together. In some embodiments, external pledgets can be moved adjacent heart tissue by sliding a sheath, catheter, or other cannulated instrument over the one or more suture ends passing through a pledget and pushing the pledget until it is at a desired location adjacent the heart. In some embodiments, a knot placement device, discussed below, can be used to push an external pledget or pledgets adjacent the heart.

In some embodiments the device can have more than four suture arms. In some embodiments, there can be more or fewer than four separate sutures with more or fewer than four suture end portions that pass through the first sheath 4 and more or fewer than four suture end portions that remain outside of the first sheath 4. It can be desirable to secure together suture end portions that were previously attached to suture arms that were approximately 180 degrees apart around the circumference of the elongate body, or suture end portions that are spaced approximately 180 degrees apart around an opening in a heart, as discussed above. When more than two pairs of suture end portions that pass through the first sheath are thus joined and pulled into the heart as illustrated in FIG. 19, the result will be a first length of suture as illustrated in FIG. 19 and two or more lengths of suture similar to the first length but rotated about an axis of the opening in the heart wall.

Determining which of the sutures running within the sheath are approximately 180 degrees apart can be done by pulling on the sutures to mechanically see which sutures runs through which point. In some embodiments, different colored sutures can be used to more easily determine which suture ends are approximately 180 degrees apart. For example, in an embodiment with four suture arms, the suture end attached to a first suture arm can be a first color and the suture end attached to a second suture arm 180 degrees about the circumference of the elongate body from the first suture arm can also be of the first color. A third suture end attached to a third arm can be of a second color, and a fourth suture end attached to a fourth arm 180 degrees about the circumference of the elongate body from the third arm can be of the second color, as well. Then, when the four suture ends run through the first sheath, the two ends of the first color can be secured together and the two ends of the second color can be secured together.

Once the suture ends that pass through the first sheath 4 have been appropriately secured and pulled into the heart, as illustrated in FIG. 19, a suturing or other surgical device can be inserted through the first sheath 4 and into the interior of the heart. In some embodiments, prior to inserting a device into the heart, it may be desirable to replace the first sheath with a different sheath. This can be done by standard procedures known in the art, and can also be done while maintaining a sheath within the opening of the heart to thereby maintain haemostasis. For example, an obturator may be slid over the first sheath 4. The sheath 4 can then be removed, and a larger sheath may be delivered over the obturator.

Once the desired procedure has been performed, the sheath can be withdrawn while tightening the sutures to close the opening around the sheath as the sheath is withdrawn. In some embodiments, a tapered sheath can be inserted prior to closing the opening, which can make it easier to close the opening tightly around the sheath as the sheath is withdrawn from the heart. In some embodiments, a knot delivery device, such as the device mentioned above and described in U.S. Patent Application Publication No. 2011/0190793 and incorporated by reference herein, can be pre-loaded with the two or more of the end portions of sutures 30 and delivered into the thoracic cavity alongside the sheath, making it easier to maintain a tightening pressure as the sheath is withdrawn. The opening in the heart can then be closed by applying or tying a knot to the suture ends or by other known methods.

Further Device Embodiments

FIG. 25 illustrates an embodiment of a device 101 that can be used to limit or prevent blood or other fluid from collecting between the heart and the pericardial sac that surrounds the heart. Many aspects of the device can function substantially the same as aspects of the device described with respect to FIGS. 1-19, even if not specifically illustrated or described with reference to the embodiment of FIG. 25. For example, the embodiment illustrated in FIG. 25 can be used with a sheath or sheaths as discussed above to place sutures through the wall of the heart and allow for performance of a procedure within the heart while maintaining or substantially maintaining haemostasis. Unless discussed otherwise, components can be considered to have substantially the same function and operate in substantially the same manner as similarly labeled components described with respect to FIGS. 1-19.

The distal end 102 of the device can have a first section 140 and a second section 142, as illustrated in FIG. 25. The device can also have one or more openings or holes 146 positioned at a distal end of the second section. The one or more openings or holes can connect to one or more lumens that run through the proximal end of the device. In some embodiments, the lumen(s) can connect to a source of negative pressure, a stopcock, a syringe, or any other device or receptacle. In some embodiments, each of the one or more openings connects to a corresponding lumen. In some embodiments, some of the one or more openings connect to the same lumen.

The first and second sections are separated by a distally facing surface 144, which can be formed from a step, notch, chamfer, bevel, or other geometry between the first and second sections whereby the second section has a larger outer dimension than the first section. In some embodiments, the second section 142 has a cross sectional area immediately adjacent the surface 144 that is greater than a cross sectional area of the first section 140 immediately adjacent the surface 144. As illustrated, the surface 144 is formed from a step between the first and second sections. The surface 144 can be at varying angles relative to the first and second sections such that in some embodiments the surface 144 is only partially distally facing, but the surface is configured such that when the first section 140 of the device enters an opening in the outer wall of a heart that is smaller than the second section 142, the surface 144 will press against the outer surface of the heart to block further entry of the device rather than expanding the opening to allow the second section 142 to enter the opening.

Figure 26:
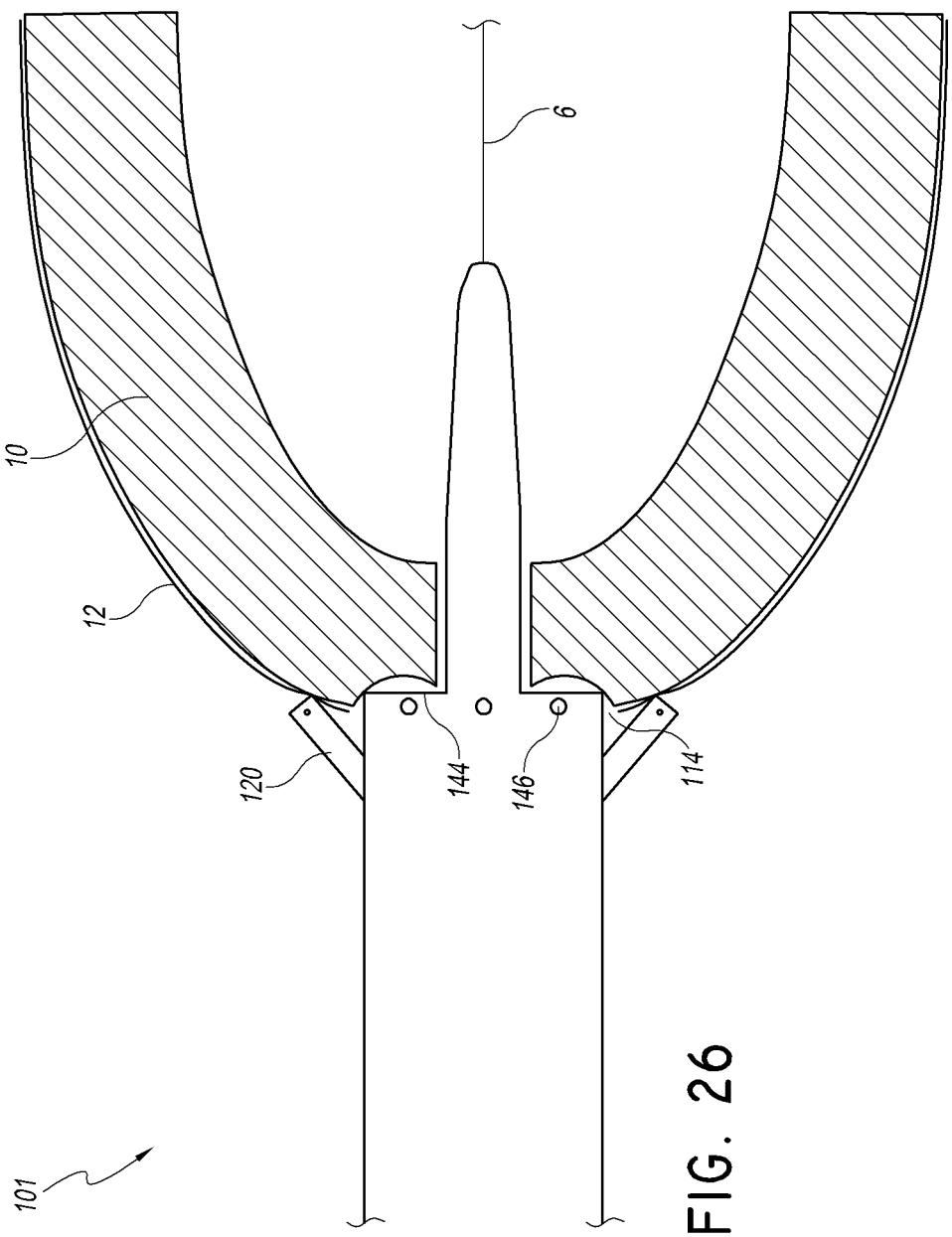
FIG. 26 is a cross sectional schematic representation of the device of FIG. 25 passing through an opening at the apex of a heart with arms extended.

This mechanism can be seen in FIG. 26, which illustrates the device after it has been inserted into the heart. In some embodiments a sheath (e.g. first sheath 4) can be delivered into the heart first and then pulled back before the device is inserted into the heart. The surface 144 has pressed against the outer wall of the heart, compressing it inward to form a gap or space 114. Blood that makes it out of the heart and into the space 114 can drain through the holes 146, either through gravity or some form of negative pressure applied to the lumen(s) that connect to the holes 146. Consequently, blood is much less likely to end up between the pericardium 12 and the heart wall 10.

As illustrated, the arms 120 of the device are extended and pressing against the pericardium 12 and wall of the heart 10. The arms extend from the device at less than a 90 degree angle, but in some embodiments the arms can extend from the device at 90 degrees. As described above, the arms can releasably retain suture portions (not shown), and the device can comprise needles that can fire through the heart wall 10 and the pericardium 12 to capture the suture portions, and then drawn them back through the tissue and into the device.

In some embodiments, it may be desired to have the sutures pass only through tissue of the heart wall, but not through the pericardium 12. The pericardium can then be left open as a drain, it can be separately sutured shut, or a drainage device can be installed near or within an opening in the pericardium and it can be sutured later. FIGS. 22 and 23 illustrate one method of using the device of FIG. 25 to pass sutures through tissue of the heart but not the pericardium.

Figure 27:
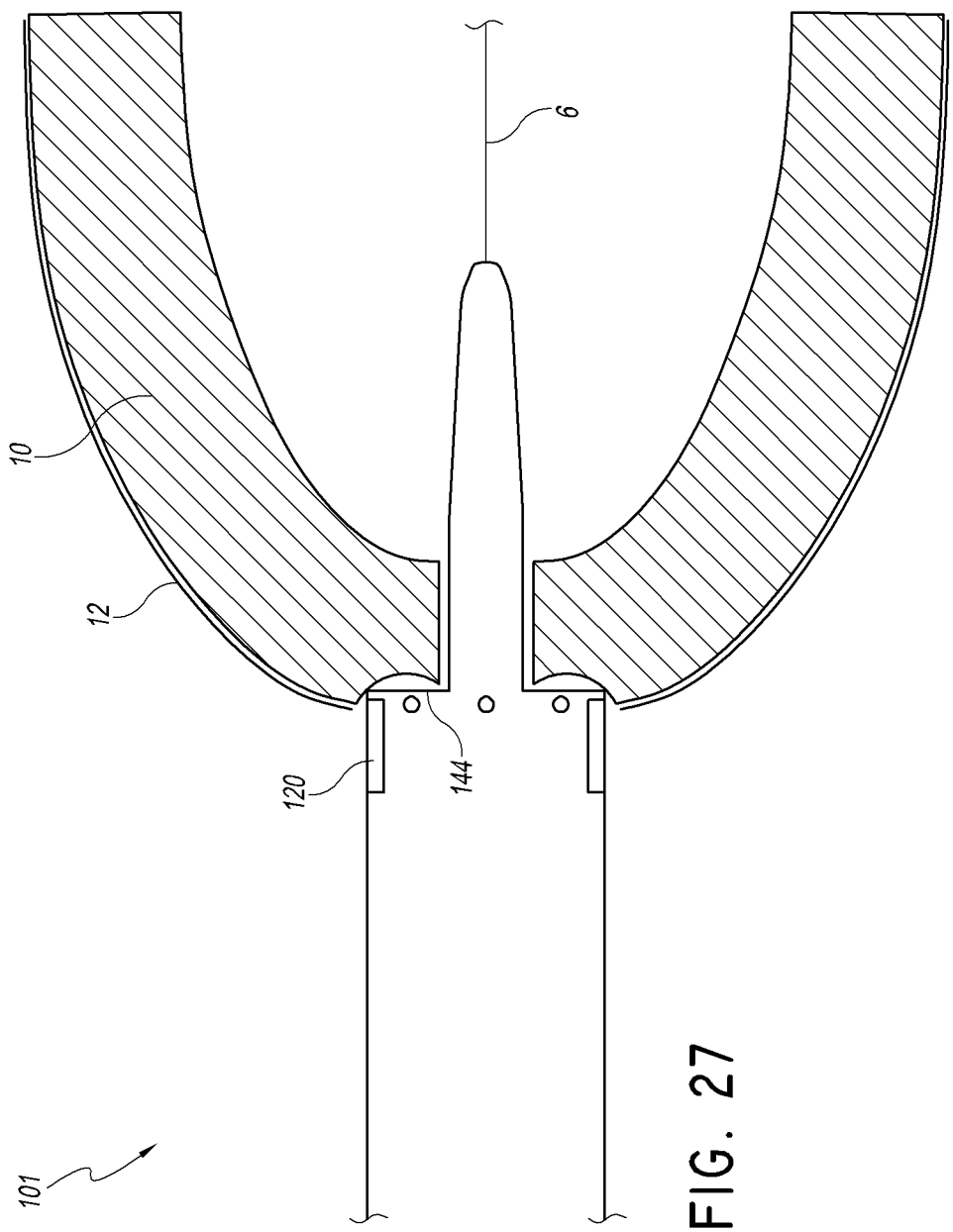
FIG. 27 is a cross sectional schematic representation of the device of FIG. 25 passing through an opening at the apex of a heart with arms retracted.

As illustrated in FIG. 27, the device can be inserted while the arms 120 remain in a retracted position until the distal ends of the arms reach a point between the pericardium 12 and an external surface of the heart wall 10. In some embodiments a sheath (e.g. first sheath 4) can be delivered into the heart first and then pulled back before the device is inserted into the heart. As illustrated, when the device has been inserted the surface 144 has begun to compress the heart wall when the distal ends of the arms are between the pericardium and the external surface of the heart wall. In some embodiments, the arms can reach that position before the surface contacts the heart wall.

Once the arms are in position they can rotate to the extended position, catching the pericardium and drawing it outward, as illustrated in FIG. 28. In some embodiments, the arms can have a hook, sharp edge, notch, or other structure on an outer surface of the arms that can engage with the pericardium and make it easier to draw the pericardium outward. Once the arms have been extended to a desired position, the device can be advanced farther into the heart until the arms are against the heart wall 10. From that position, any of the procedures discussed with reference to FIGS. 10-24B can be used.

Although the foregoing description of the preferred embodiments has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures or characteristics of any embodiment described above may be combined in any suitable manner, as would be apparent to one of ordinary skill in the art from this disclosure, in one or more embodiments.

Similarly, it should be appreciated that in the above description of embodiments, various features of the inventions are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A method of delivering suture portions to an opening in a heart wall of a patient, the method comprising:
   delivering a suturing system through the heart wall, wherein the suturing system comprises:
      a suturing device comprising an elongate body having a proximal end and a distal end, the suturing device having a distal section that extends through the heart wall and into the heart once the suturing system is delivered, the suturing device comprising a plurality of arms positioned outside of the heart and a plurality of needles positioned inside the heart once the suturing system is delivered;
      a first sheath positioned over the suturing device, a distal end of the first sheath being proximal to the plurality of arms once the suturing system is delivered; and
      a second sheath positioned over the first sheath;
   extending the plurality of arms from the elongate body of the suturing device, each of the arms carrying a suture portion having a suture end releasably retained in a respective arm, wherein each suture portion extends from its respective arm proximally between the first sheath and the second sheath to a location outside of the patient;
   positioning the plurality of arms against the outside surface of the heart;
   advancing the plurality of needles from the elongate body through the heart wall, each needle aligned with a respective arm and engaging a respective suture end carried by the respective arm;
   retracting the plurality of needles through the heart wall to draw the respective suture ends through the heart wall;
   retracting the arms into the elongate body of the suturing device while maintaining a distal section of the elongate body within the heart;
   advancing the first sheath positioned around the elongate body into the opening in the heart wall; and
   withdrawing the elongate body from the heart wall while leaving the first sheath within the heart wall, the withdrawing of the elongate body drawing the suture ends engaged by the needles through a lumen of the first sheath to a location outside of the patient.

2. The method of claim 1, further comprising removing the second sheath from around the first sheath after withdrawing the elongate body.

3. The method of claim 1, further comprising joining a pair of suture portions extending through the first sheath, thereby forming a single suture.

4. The method of claim 3, further comprising pulling on one or both of the remaining free ends of the single suture to remove the single suture from the first sheath and provide a continuous length of suture extending into the heart and across the opening in the heart wall.

5. The method of claim 4, further comprising attaching a pledget to one or both of the suture portions before joining the pair of suture portions, wherein pulling on one or both of the remaining free ends comprises pulling on one of the free ends until the pledget enters the heart.

6. The method of claim 4, further comprising performing one or more procedures on the heart with the suture extending into the heart and across the opening of the heart wall.

7. The method of claim 6, further comprising using said suture to close the opening in the heart wall after the one or more procedures on the heart are performed.

8. The method of claim 4, further comprising tightening the single suture while withdrawing the first sheath, thereby closing the opening in the heart as the first sheath is withdrawn to substantially maintain haemostasis within the heart.

9. The method of claim 1, wherein the plurality of arms comprises a first arm and a second arm positioned approximately 180 degrees apart from the first arm around a circumference of the elongate body.

10. The method of claim 1, further comprising attaching a pledget to one of the suture ends and pulling a suture portion such that the pledget is within the heart.

11. The method of claim 1, wherein the suturing device comprises four arms, and further comprising joining a first and second pair of suture portions extending through the first sheath, thereby forming a pair of separate sutures.

12. The method of claim 11, further comprising attaching a first pledget to one of the sutures of the first pair of suture portions prior to joining the sutures of the first pair, and attaching a second pledget to one of the sutures of the second pair of suture portions prior to joining the sutures of the second pair.

13. The method of claim 12, further comprising attaching the first pledget to one of the sutures of the second pair of suture portions prior to joining the sutures of the first and second pairs, and attaching the second pledget to a separate one of the sutures of the first pair of suture portions prior to joining the sutures of the first and second pairs.

14. The method of claim 1, comprising, prior to delivering the suturing system through the heart wall:
  delivering a trocar through a patient's chest to provide access to the thoracic cavity;
  delivering a hollow needle through the trocar and into the heart through a heart wall;
  delivering a guidewire through the trocar and through the hollow needle into the heart;
  removing the hollow needle;
  wherein the suturing system is delivered through the trocar into the thoracic cavity and over the guidewire into the heart.

15. A method of performing a procedure on the heart of a patient, the method comprising:
  delivering an elongate device through a heart wall such that a distal section of the device is positioned within the heart, wherein the elongate device is a suturing device comprising a plurality of arms and a plurality of needles;
  removing fluid exiting the heart along the distal section of the elongate device and through the heart wall, said removing of fluid comprising causing said fluid to flow through at least one opening positioned on the elongate device on an outside of the heart to remove fluid that may accumulate between the outside of the heart and the pericardial sac;
  moving the plurality of arms from a first position wherein the arms are retracted within the elongate device to a second position wherein the arms each have a free end extending away from the elongate device and are positioned adjacent an outer surface of the heart, each arm comprising at least one suture mount at the free end releasably retaining a suture portion; and
  moving the plurality of needles from a retracted position in which the needles are within the elongate device to a deployed position in which distal points of the needles extend out of the elongate device, through the heart wall and into a suture mount of a corresponding arm.

16. The method of claim 15, wherein fluid flows through the at least one opening by applying negative pressure to the at least one opening from outside of the patient.

17. The method of claim 15, wherein the elongate device comprises a distally facing surface in its distal section, and delivering the elongate device comprises pushing the distal facing surface against the outer surface of the heart.

18. The method of claim 17, wherein the elongate device comprises a plurality of openings proximal to the distally facing surface.

19. The method of claim 15, wherein the plurality of arms are in the second position while fluid is removed.

20. A method of suturing an opening in the heart of a patient, the method comprising:
  delivering a suturing device comprising an elongate body through a heart wall such that a distal section of the device is positioned within the heart, the suturing device comprising a plurality of arms and a plurality of needles; and
  moving the plurality of arms from a first position wherein the arms are retracted within the elongate body to a second position wherein the arms each has a free end extending away from the elongate body, wherein the arms engage the pericardial sac as they move to their second positions to move the pericardial sac away from an outer surface of the heart, each arm comprising at least one suture mount at the free end releasably retaining a suture portion; and
  moving a plurality of needles from a retracted position in which needles are within the elongate body to a deployed position in which distal points of the needles extend out of the elongate body, through the heart wall and into a suture mount of a corresponding arm.

21. A method of closing an opening in the heart with sutures, the method comprising:
  inserting four sutures through tissue of a heart wall such that each suture has an end that runs through an opening in the heart and an end that runs outside of the heart, wherein the four sutures comprise a first pair and a second pair of sutures, the sutures of the first pair positioned opposite each other with respect to the opening in the heart and the sutures of the second pair positioned opposite each other with respect to the opening in the heart;
  attaching a first end of a first pledget to a first end of a first suture and attaching a first end of a second pledget to a first end of a second suture, wherein the first pair comprises the first suture and a third suture with a first end, and the second pair comprises the second suture and a fourth suture with a first end;

securing together the ends of the first pair that run through the opening in the heart;

securing together the ends of the second pair that run through the opening in the heart; and pulling on at least one of the ends of each pair that run outside of the heart.

22. The method of claim 21, further comprising attaching a second end of the first pledget to the first end of the third suture and attaching a second end of the second pledget to the first end of the fourth suture, prior to securing together the ends of the first suture pair that run through the opening in the heart and the ends of the second suture pair that run through the opening in the heart.

23. The method of claim 21, further comprising attaching a second end of the first pledget to the first end of the fourth suture and attaching a second end of the second pledget to the first end of the third suture, prior to securing together the ends of the first suture pair that run through the opening in the heart and the ends of the second suture pair that run through the opening in the heart.

24. The method of claim 21, wherein the first end of each suture is the end that runs through the opening in the heart, and the end of each suture than runs outside of the heart is a second end.

25. The method of claim 24, further comprising attaching a third pledget to the second ends of the first and fourth sutures and a fourth pledget to the second ends of the second and third sutures.

26. The method of claim 25, further comprising pushing the third and fourth pledgets to a position adjacent an external wall of the heart.

27. The method of claim 24, further comprising attaching a third pledget to the second ends of the first and third sutures and a fourth pledget to the second ends of the second and fourth sutures.

28. The method of claim 27, further comprising pushing the third and fourth pledgets to a position adjacent an external wall of the heart.

* * * * *